United States Patent
Emil et al.

(10) Patent No.: US 11,596,452 B2
(45) Date of Patent: Mar. 7, 2023

(54) SURGICAL INSTRUMENTS AND METHODS FOR SELECTIVELY COUPLING TO AN OBJECT

(71) Applicant: Medos International Sarl, Le Locle (CH)

(72) Inventors: Cory Emil, Milton, MA (US); Richard Fournier, New Bedford, MA (US); Eric Biester, Barrington, RI (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 0 days.

(21) Appl. No.: 17/164,979

(22) Filed: Feb. 2, 2021

(65) Prior Publication Data
US 2022/0240989 A1    Aug. 4, 2022

(51) Int. Cl.
*A61B 17/70*    (2006.01)
*A61B 17/00*    (2006.01)
*A61B 17/56*    (2006.01)

(52) U.S. Cl.
CPC ...... *A61B 17/7074* (2013.01); *A61B 17/7082* (2013.01); *A61B 17/7086* (2013.01); *A61B 17/7091* (2013.01); *A61B 2017/0046* (2013.01); *A61B 2017/00477* (2013.01); *A61B 2017/564* (2013.01)

(58) Field of Classification Search
CPC .............. A61B 17/7074; A61B 17/7076–7082
See application file for complete search history.

(56) References Cited

U.S. PATENT DOCUMENTS 7,179,261 B2    2/2007  Sicvol et al.
8,784,431 B1 *  7/2014  Harder ............... A61B 17/7082
                                              606/104

(Continued)

FOREIGN PATENT DOCUMENTS

EP       2896378 A1    7/2015
WO    2008134758 A1   11/2008

OTHER PUBLICATIONS

International Search Report and Written Opinion for Application No. PCT/EP2022/052493, dated May 31, 2022 (13 pages).

*Primary Examiner* — Eduardo C Robert
*Assistant Examiner* — Michelle C Eckman
(74) *Attorney, Agent, or Firm* — Barnes & Thornburg LLP

(57) ABSTRACT

Instruments and methods for selectively coupling to an object are provided, for example surgical instruments that can form a rigid connection with an object and also be disassembled for cleaning, sterilization, etc. One embodiment includes an elongate shaft with a longitudinal groove, a first partial circumferential groove that intersects with a distal end of the longitudinal groove, and a second at least partial circumferential groove formed distal to the first partial circumferential groove. The instrument also includes a sleeve disposed over the elongate shaft that includes a protrusion extending from an internal wall that is received within the longitudinal groove to constrain movement of the sleeve relative to the elongate shaft. The sleeve further includes a lock that interfaces with the second at least partial circumferential groove when the protrusion is disposed in the first partial circumferential groove to further selectively constrain axial and rotational movement of the sleeve.

25 Claims, 13 Drawing Sheets

(56) References Cited

U.S. PATENT DOCUMENTS

| | | | |
|---|---|---|---|
| 2004/0147937 A1* | 7/2004 | Dunbar, Jr. | A61B 17/7091 606/99 |
| 2006/0036255 A1 | 2/2006 | Pond et al. | |
| 2008/0045956 A1 | 2/2008 | Songer et al. | |
| 2008/0243190 A1* | 10/2008 | Dziedzic | A61B 17/7091 606/278 |
| 2013/0282019 A1* | 10/2013 | Bouliane | A61B 17/8888 606/104 |
| 2015/0201987 A1* | 7/2015 | Lemoine | A61B 17/8891 606/104 |
| 2015/0282855 A1* | 10/2015 | Bess | A61B 17/7082 606/86 A |
| 2016/0296266 A1* | 10/2016 | Chandanson | B25B 23/0035 |
| 2018/0177536 A1* | 6/2018 | Divincenzo | A61B 17/7091 |
| 2018/0368892 A1 | 12/2018 | Marnay | |

\* cited by examiner

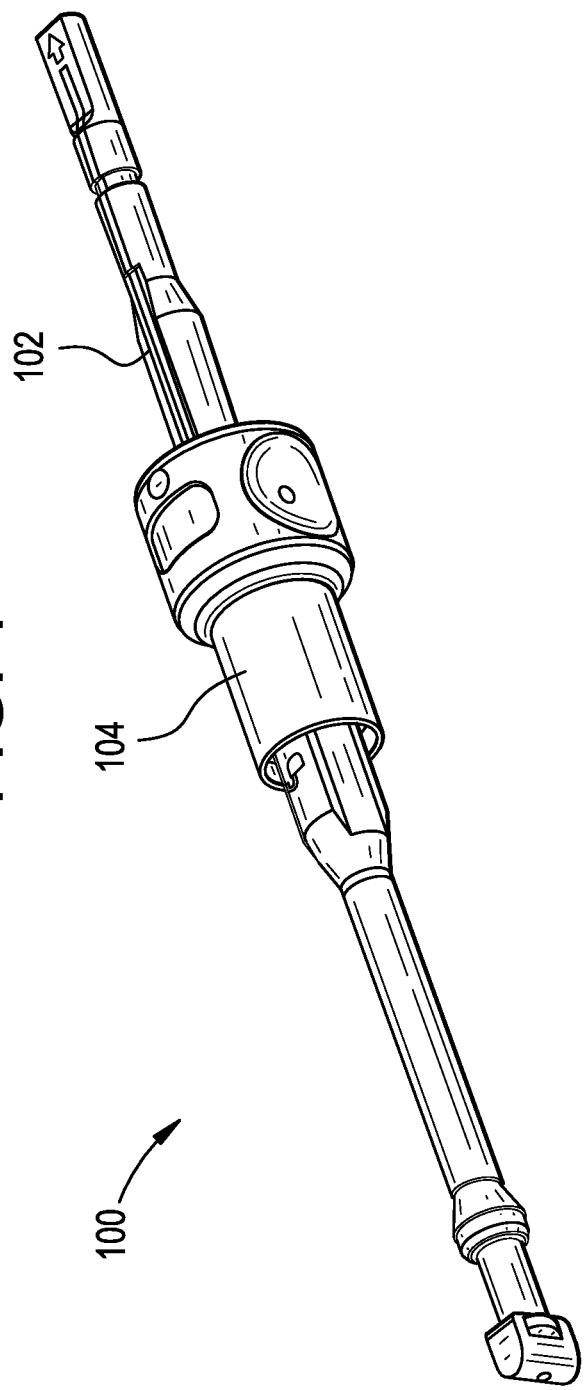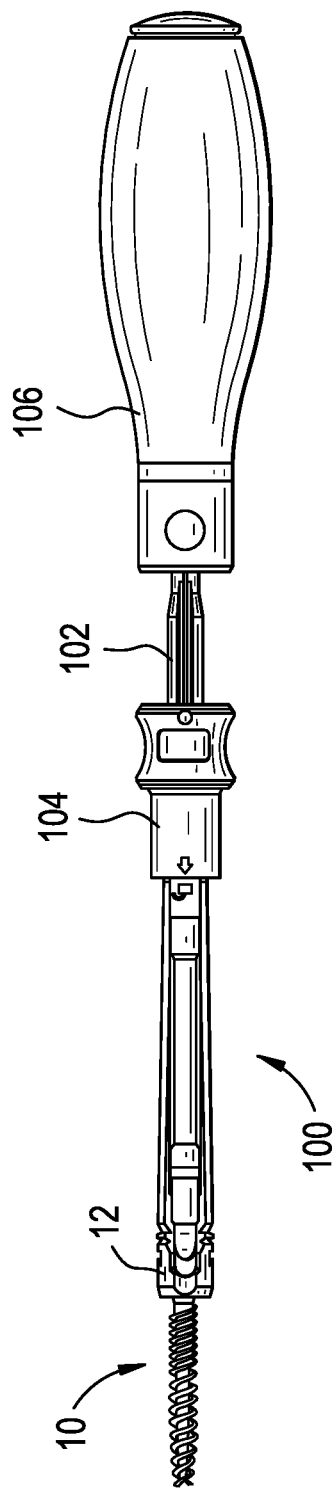

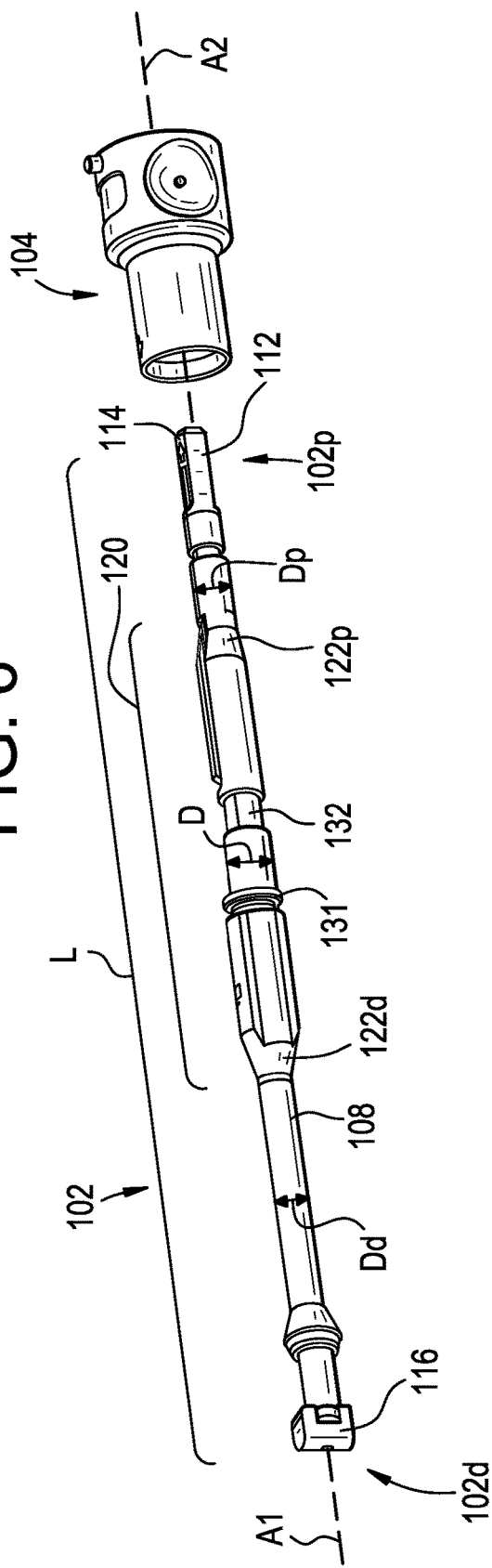

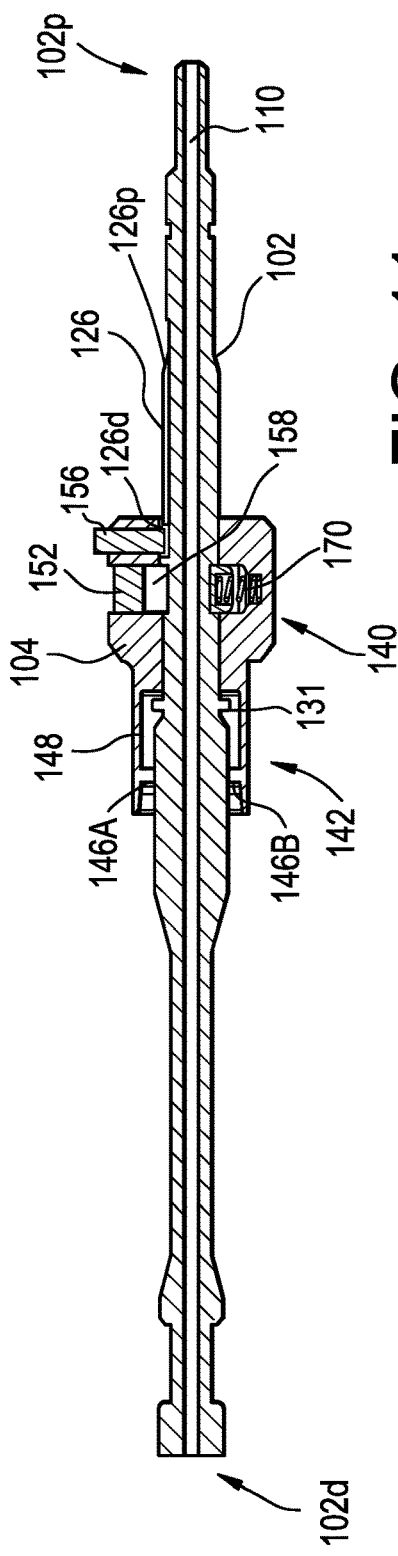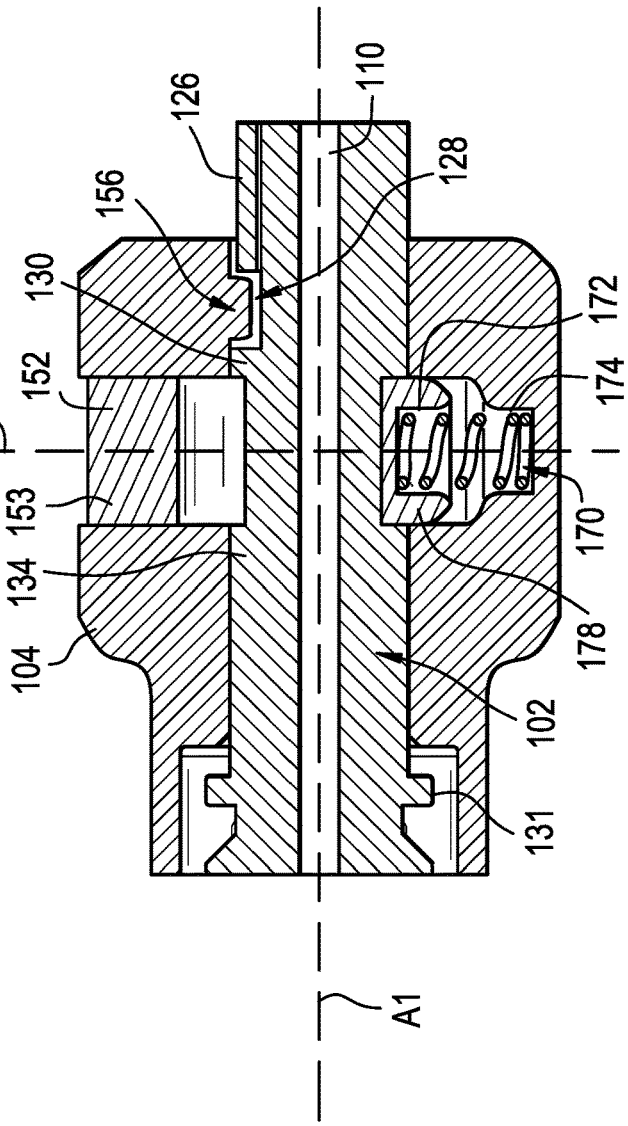

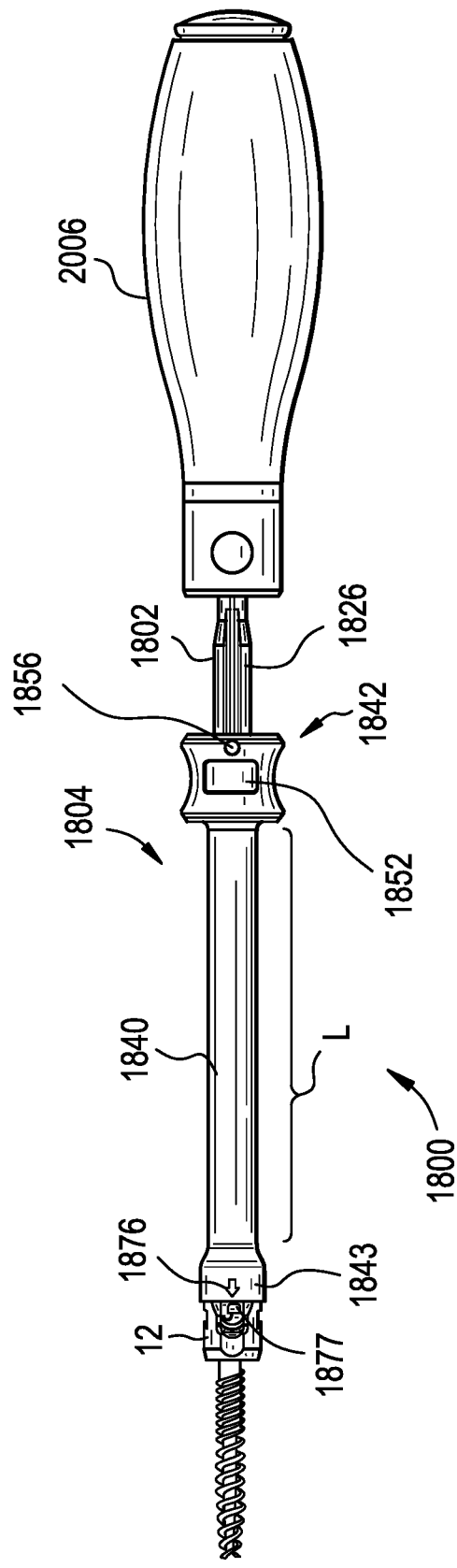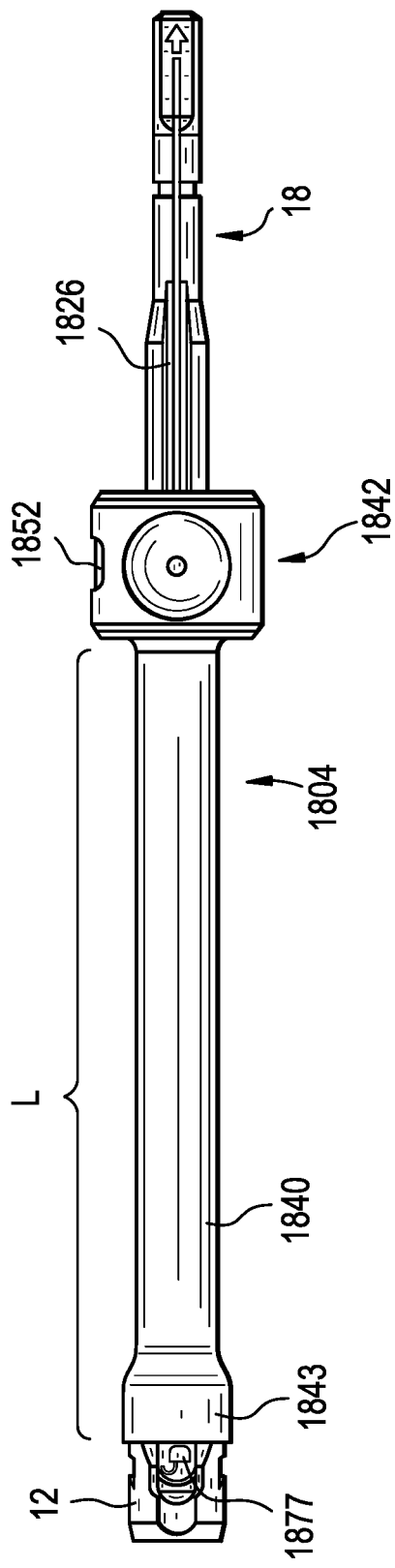

SURGICAL INSTRUMENTS AND METHODS FOR SELECTIVELY COUPLING TO AN OBJECT

FIELD

The present disclosure relates to instruments and methods for selectively coupling to an object, for example surgical instruments that can form a rigid connection with an object during a surgical procedure and later be disassembled for cleaning, sterilization, etc.

BACKGROUND

Various surgical procedures can require one or more instruments that selectively couple to another object for use during a procedure. For example, in minimally invasive procedures various elongate instruments can be coupled to other objects, such as various implants, anchors, etc., and utilized to pass the objects to a surgical site and manipulate them from a remote location. In some cases, such instruments can be required to impart significant forces to an object coupled thereto, e.g., significant axial forces of tension or compression, as well as rotational forces in certain cases. Further, certain instruments can include multiple components that can be selectively moved relative to one another, such as components that rotate relative to one another to selectively lock to an object, etc.

Still further, surgical instruments used in an operating room environment can be subject to cleaning requirements that necessitate a design that enables disassembly for sterilization, etc. The need for utilizing components that can be disassembled can be in conflict with requirements for the instruments to achieve desired selective coupling with an object, such as forming a rigid connection with an implant to impart the above-mentioned forces, etc.

One example of this tension can be found when assembling modular receiver heads to bone screw shanks intraoperatively, though a variety of other examples also exist. Modular bone anchors can be desirable in surgical operations because a surgeon or other user can implant a screw shank without any spinal fixation element (e.g., rod) receiving head being attached thereto, which can afford the surgeon a better view of the implantation site and allow for use of lower profile instrumentation. Once the screw shank is implanted, the modular receiver head can be coupled thereto using an inserter instrument. The instrument can require a selective rigid connection to the modular receiver head such that the instrument can be utilized to impart significant forces during implantation and positioning of the bone anchor. A competing concern, however, is that the inserter instrument also be easily cleaned/sterilized, which often means providing for disassembly of the instrument into various parts. This can involve instrument components that can rotate relative to one another and lock in one or more positions but be separable when desired. Prior instruments configured for such use often fail to provide sufficiently rigid connection to an object due to play and tolerancing in the various interfaces between components of the instruments.

Accordingly, there is a need for improved instruments and methods that provide selective coupling to an object, such as a selectively rigid connection therebetween, while allowing for disassembly of instrument components for cleaning and sterilization.

SUMMARY

The present disclosure provides examples of surgical instruments that address the challenges noted above. For example, the embodiments described herein can provide surgical instruments with multiple components capable of disassembly and relative movement for configuration changes (e.g., coupling/decoupling to various objects, etc.) but can provide desired selective coupling (e.g., a rigid connection) to another object. Certain embodiments described herein are particularly adapted to coupling with modular receiver heads used during spinal fixation procedures, but the features of the disclosed embodiments can also be utilized with other types of instruments used in various other surgical procedures.

In one aspect, a surgical instrument is disclosed that includes an elongate shaft having a longitudinal groove formed along a portion thereof, a first partial circumferential groove that intersects with a distal end of the longitudinal groove, and a second at least partial circumferential groove formed distal to the first partial circumferential groove. The instrument further includes a sleeve configured to be disposed over the elongate shaft, the sleeve including a protrusion extending from an internal wall thereof that is configured to be received within the longitudinal groove of the elongate shaft to constrain movement of the sleeve relative to the shaft when the sleeve is disposed over the elongate shaft. Further, the sleeve includes a lock configured to interface with the second at least partial circumferential groove when the protrusion is disposed in the first partial circumferential groove to further selectively constrain both axial and rotational movement of the sleeve relative to the shaft.

The instruments and methods described herein can have a number of additional features and/or variations, all of which are within the scope of the present disclosure. For example, in some embodiments the lock can include a button disposed within a recess of the sleeve and configured to translate radially relative to the sleeve and elongate shaft between a locked position and an unlocked position. The button can, in some cases, be biased toward the locked position. In some embodiments, the button can include a through-bore configured to receive the elongate shaft therethrough.

In certain embodiments, the second at least partial circumferential groove can include a plurality of flat portions angularly offset from one another to define a plurality of rotational positions of the shaft relative to the sleeve. In some embodiments, for example, the plurality of flat portions can include a first flat portion and a second flat portion that define first and second rotational positions of the shaft relative to the sleeve. The lock can, in some cases, include a flat portion configured to abut one of the plurality of flat portions of the second at least partial circumferential groove to maintain the shaft at one of the plurality of rotational positions relative to the sleeve.

In some embodiments, the instrument can further include a handle configured to couple to a proximal portion of the elongate shaft to facilitate manipulation of the instrument. And in certain embodiments, the sleeve and the elongate shaft can be configured to engage one or more objects therebetween to form a rigid connection with the one or more objects. For example, in some cases, the sleeve can further include a pair of arms to engage the objects when disposed between the elongate shaft and the sleeve. The object can be any of a variety of objects utilized in various surgical procedures. For example, in some embodiments the object can include one or more extended tabs of a receiver head.

In another aspect, a surgical instrument is disclosed that includes an elongate shaft having a longitudinal groove formed along a portion thereof, a first partial circumferential groove that intersects with a distal end of the longitudinal groove, and a second circumferential groove formed distal to the first partial circumferential groove. The instrument further includes a sleeve configured to be disposed over the elongate shaft and a pin configured to be received within a through-bore of the sleeve such that the pin extends into an inner lumen of the sleeve and can be received in the longitudinal groove and first partial circumferential groove of the elongate shaft to constrain relative movement of the sleeve and the elongate shaft when the sleeve is disposed over the elongate shaft. The instrument further includes a button received within a recess of the sleeve and configured to translate radially relative thereto. The button includes a through-bore formed therein that is configured to receive the elongate shaft therethrough when the sleeve is disposed over the elongate shaft. Further, the button is configured to be disposed within the second circumferential groove of the elongate shaft and further constrain relative movement of the elongate shaft and sleeve when the pin is received in the first partial circumferential groove of the elongate shaft.

As noted above, any of a variety of additional features and/or variations are possible and within the scope of the present disclosure. For example, in some embodiments, the sleeve can further include first and second partial circumferential protrusions formed on a wall of the inner lumen of the sleeve. And in certain embodiments, the button can be biased radially outward relative to the sleeve.

In some embodiments, the second circumferential groove can include a plurality of flat portions angularly offset from one another to define a plurality of rotational positions of the shaft relative to the sleeve. For example, in some embodiments the plurality of flat portions can include a first flat portion and a second flat portion that define first and second rotational positions of the shaft relative to the sleeve. The button can, in some embodiments, include a flat portion configured to abut one of the plurality of flat portions of the second circumferential groove to maintain the shaft at one of the plurality of rotational positions relative to the sleeve.

In certain embodiments, the sleeve and the elongate shaft can be configured to engage one or more objects therebetween to form a rigid connection with the one or more objects. Such objects can include, for example, opposed arms of a receiver head used for spinal fixation, though other objects utilized in different procedures are also possible.

In another aspect, a method for coupling an instrument to an object is disclosed that includes advancing a sleeve over an elongate shaft such that a protrusion extending from an internal wall of the sleeve travels within a longitudinal groove formed in the elongate shaft. The method further includes positioning an object such that a portion of the object is disposed between the sleeve and the elongate shaft. The method also includes rotating the sleeve relative to the elongate shaft such that the protrusion travels within a partial circumferential groove formed in the elongate shaft that intersects with a distal end of the longitudinal groove to prevent relative movement between the object and the instrument.

As with the aspects disclosed above, any of a variety of additional steps and/or variations are possible and within the scope of the present disclosure. For example, in some embodiments, positioning the object can include contacting the object with a pair of arms extending from the sleeve.

In certain embodiments, the sleeve can be advanced over the elongate shaft to a position where the protrusion is disposed at an intersection of the longitudinal groove and the partial circumferential groove, and a lock of the sleeve can be disposed in a second at least partial circumferential groove formed in the elongate shaft distal to the partial circumferential groove. Further, in some embodiments the second at least partial circumferential groove can include a plurality of flat portions angularly offset from one another to define a plurality of rotational positions of the shaft relative to the sleeve, the lock can include a flat portion configured to abut one of the plurality of flat portions of the second at least partial circumferential groove to maintain the shaft at one of the plurality of rotational positions relative to the sleeve, and rotating the sleeve relative to the elongate shaft can include rotating the sleeve between a first of the plurality of rotational positions and a second of the plurality of rotational positions. In other embodiments, the method can further include actuating the lock of the sleeve to move the lock out of the second at least partial circumferential groove formed in the elongate shaft.

Any of the features or variations described above can be applied to any particular aspect or embodiment of the present disclosure in a number of different combinations. The absence of explicit recitation of any particular combination is due solely to the avoidance of repetition in this summary or elsewhere in this disclosure.

BRIEF DESCRIPTION OF DRAWINGS

This invention will be more fully understood from the following detailed description taken in conjunction with the accompanying drawings, in which:

FIG. 1 is a front perspective view of one embodiment of a modular implant inserter;

FIG. 2 is a side view of the modular implant inserter of FIG. 1 mated to a bone anchor and handle;

FIG. 6 is an exploded perspective view of the device of FIG. 1;

FIG. 7 is a partially-transparent detail top view of the device of FIG. 1;

FIG. 10 is a side cross-sectional view of the device of FIG. 1 in an unlocked position;

FIG. 11 is a detail side cross-sectional view of the device of FIG. 1 in an unlocked position;

FIG. 20 is a top view of the device of FIG. 18 in an unlocked configuration and positioned to couple with a polyaxial bone anchor like that shown in FIG. 3;

FIG. 21 is a top view of an elongate shaft and a sleeve assembly of the device of FIG. 18 in a locked position coupled to a modular receiver member like that shown in FIG. 3.

DETAILED DESCRIPTION

Figure 3:
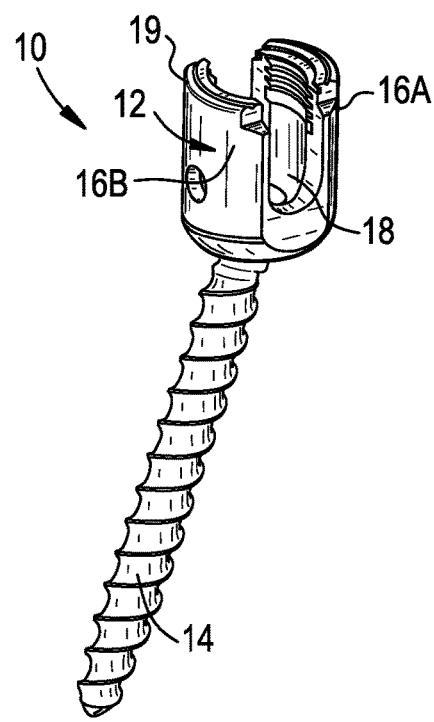
FIG. 3 is a perspective view of a bone anchor assembly.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting example embodiments and that the scope of the present invention is defined solely by the claims. The features illustrated or described in connection with one embodiment may be combined with the features of other embodiments. Such modifications and variations are intended to be included within the scope of the present disclosure.

Instruments and methods for assembly of modular implants are generally provided. In particular, the instruments and methods disclosed herein allow for formation of rigid connections with parts of an implant to enable intraoperative assembly of implant parts, e.g., bone anchors. During assembly of the implant, the instrument can impart one or more forces onto the implant parts to secure the parts to one another. For example, the instrument can rigidly connect to an implant part and manipulate the part relative to other implant parts to modularly assemble the implant. The instrument can include multiple components that can move independently relative to one another, as well as relative to other implant parts, to lock the instrument in one or more positions. The components can be selectively disassembled such that one or more of the components can be cleaned and/or replaced.

A variety of devices and methods are disclosed herein. Some devices include spinal implants configured to be disposed between adjacent vertebrae. Other devices include spinal fixation elements that can be configured to extend from one vertebra to one or more additional vertebrae, even if those vertebrae are not adjacent. The disclosed methods include surgical techniques that allow implants to be disposed through a small incision that is positioned laterally, anteriorly, or posterior-laterally on a subject being treated. In the present disclosure, like-numbered components of the embodiments generally have similar features, and thus within a particular embodiment each feature of each like-numbered component is not necessarily fully elaborated upon. Further, to the extent that linear or circular dimensions are used in the description of the disclosed devices and methods, such dimensions are not intended to limit the types of shapes that can be used in conjunction with such devices and methods. Equivalents to such linear and circular dimensions can be determined for any geometric shape. Sizes and shapes of each device, and the components thereof, can depend at least on the anatomy of the subject in which the devices will be used and the size and shape of components with which the devices will be used.

FIG. 1 illustrates one embodiment of an instrument 100 that connects to modular structures, e.g., implant parts, to couple said structures to various devices. For example, the instrument 100 can generally be used to assemble modular spinal fixation element receiver members or heads to shanks, e.g., bone screw shanks, intraoperatively and/or in-situ. The instrument 100 can selectively form a rigid connection with an implant by engaging one or more implant parts. As shown, the instrument 100 can attach to a modular component, e.g., opposing arms or extended tabs of a receiver member, to enable transmission of tensile and compressive forces during selective attachment of said modular component to another structure, thereby forming an implant.

The instrument 100 can include an assembly of an elongate shaft 102 and a sleeve or sleeve assembly 104. The instrument can further couple to a handle 106, as shown in FIG. 2. As shown in FIGS. 1 and 2, the elongate shaft 102 can be received within the sleeve 104 and can allow for selective independent movement therebetween. The configuration of the elongate shaft 102 and the sleeve 104 can be manipulated relative to one another to provide for multiple configurations, e.g., unlocked and locked positions of the instrument 100, as discussed in further detail below. The instrument 100 can engage one or more modular parts, e.g., a receiver member, to enable assembly of these modular parts to form an implant. The handle 106 can be coupled to the elongate shaft 102 to facilitate manipulation of the instrument and/or movement of the instrument between the unlocked and locked positions.

Figure 4:
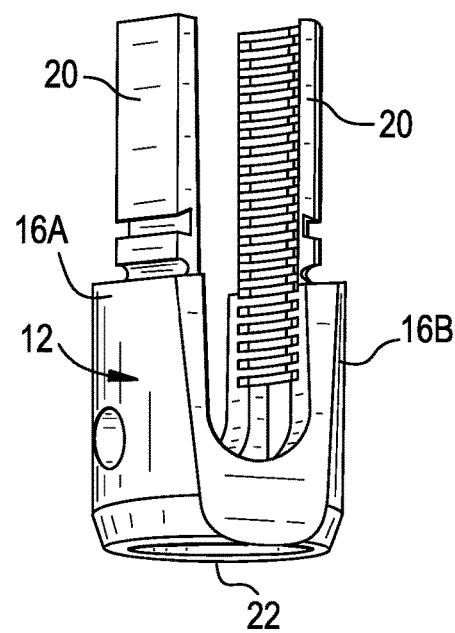
FIG. 4 is a perspective view of a modular receiver member of a bone anchor assembly with extension tabs.
Figure 5:
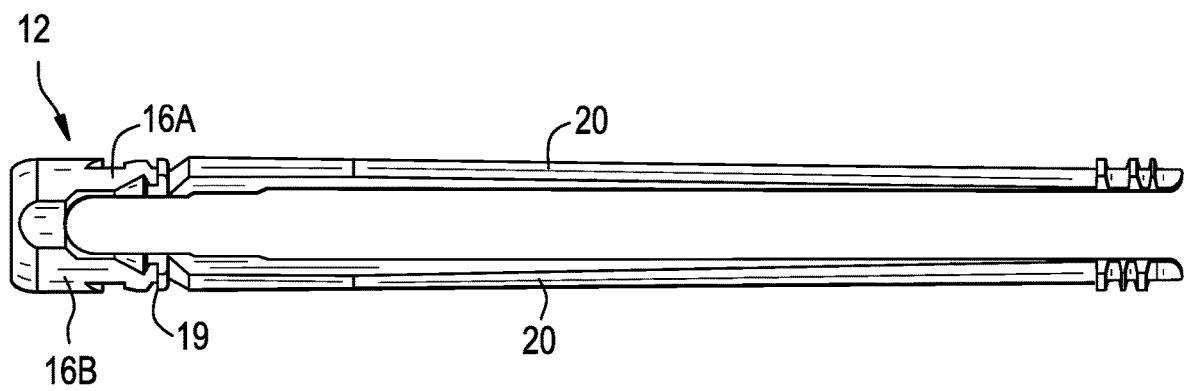
FIG. 5 is a side view of another modular receiver member of a bone anchor assembly with extension tabs.

FIGS. 3-5 illustrate exemplary embodiments of modular parts with which the instruments disclosed herein can be used. It will be appreciated that the illustrated modular parts are examples and that other modular parts having additional or alternative features, which do and do not pertain to implants used within the body of a patient, can be used with the instruments disclosed herein.

The instrument 100 can be coupled to a bone anchor assembly 10. The illustrated bone anchor assembly 10 can include a receiver member or head 12 for receiving a spinal fixation element, such as a spinal rod (not shown), to be coupled to a bone shank 14 for implantation into the body of a patient. The receiver member 12 can include a proximal end having a pair of spaced apart arms 16A, 16B defining a recess 18 therebetween and a distal end having a distal end surface defining an opening 22 (see FIG. 4) through which at least a portion of the bone shank 14 can extend. The bone shank 14 can be configured to engage bone and, in the illustrated embodiment, includes an external bone engaging thread.

The shape of the receiver member 12 can vary. For example, the receiver member 12 can be generally cylindrical in shape with planar proximal and distal surfaces and rounded corners at least at the distal end. Each of the pair of spaced apart arms 16A, 16B can extend from the distal end of the receiver member 12 toward a free proximal end. The outer surfaces of each of the arms 16A, 16B can include a feature, such as a recess, dimple, notch, projection, or the like, to facilitate connection of the receiver member 12 to instruments, e.g., instruments of the type described herein. For example, the outer surface of each arm 16A, 16B can include an arcuate groove 19 at the respective free end of the arms. Such grooves are described in more detail in U.S. Pat. No. 7,179,261, issued on Feb. 20, 2007, which is hereby incorporated by reference herein.

The pair of spaced apart arms 16A, 16B can vary in size. For example, in some embodiments the pair of spaced apart arms 16A, 16B can be designed for implantation into the body of the patient (e.g., as shown in FIG. 3). In some embodiments, as shown in FIGS. 4 and 5, the receiver member 12 can include, e.g., be formed integrally with or coupled to, one or more extension tabs 20 that extend proximally from the receiver member 12 to functionally extend the length of the arms 16A, 16B. The length of these extension tabs 20 can vary, e.g., as shown in FIGS. 4 and 5, and can be used to aid positioning of the head, reduction of fixation rods, introduction of rod-locking fixation elements such as set screws, etc.

In use, the instrument can be positioned such that one or more of the pair of spaced apart arms 16A, 16B of the receiver member 12 are received between the elongate shaft 102 and the sleeve 104 to dock the instrument 100 to the receiver member 12, e.g., as shown in FIG. 2. The sleeve 104 can be movable between an unlocked position and a locked position to lock the instrument 100 to the receiver member 12. For example, the sleeve 104 can be rotated or axially translated relative to the elongate shaft 102 to selectively prevent the pair of spaced apart arms 16A, 16B from separating from the instrument 100, thereby retaining the receiver member 12 to the instrument 100. The instrument can enable the delivery of axial loads and the transmission of tensile and compressive forces to the receiver member 12 to assemble the bone anchor assembly 10 by coupling the receiver member 12 to a bone anchor shank 14. After assembly, the instrument 100 can decouple from the bone anchor assembly 10 and the elongate shaft 102 and the sleeve 104 can be disassembled for cleaning.

FIGS. 6-15 illustrate an assembly of the elongate shaft 102 and the sleeve 104 of the instrument 100, as well its operation. The elongate shaft 102 can include a generally tubular body 108 having a central longitudinal axis A1 that extends along a length L of the tubular body 108 from a proximal end 102p to a distal end 102d. The elongate shaft 102 can include an inner channel 110 (see FIG. 10) that extends along the central longitudinal axis A1 of the shaft 102 from the proximal end to the distal end, though, in some embodiments, the elongate shaft 102 can have a solid core therethrough. The elongate shaft 102 can transmit forces to an implant mated thereto, e.g., the bone anchor assembly 10.

The proximal end 102p of the elongate shaft 102 can be sized to be received within the sleeve 104. The proximal end 102 can include a tab 112 that can pass through a lumen of the sleeve 104 to advance the elongate shaft 102 therethrough. As shown, the tab 112 can include an interface 114 that can couple the elongate shaft 102 to other components of the instrument 100, e.g., the handle 106. The interface can be keyed such that it is received in the handle 106 in one or more specific orientations.

The distal end 102d of the elongate shaft 102 can include a coupler 116. In some embodiments, the coupler 116 can be received between the pair of spaced apart arms 16A, 16B to impart a force onto the receiver member 12 coupled to the instrument 100 and to prevent unintended rotation of the receiver member 12 relative to the instrument. The coupler 116 can be in the form of a block, as shown, though, in some embodiments, the coupler 116 can be a tube, a pair of arms, or a spring configured to facilitate impartation of a force and/or securing an object to the instrument 100.

The tubular body 108 can include one or more sections having different diameters. For example, the elongate shaft 102 can include an intermediate portion 120 disposed between the proximal and distal ends 102p, 102d. As shown, the intermediate portion 120 can be a portion of the tubular body 108 that tapers down to one or more of the proximal and distal ends 102p, 102d. For example, the intermediate portion can taper towards the distal end 102d at a distal juncture 122d and can taper towards the proximal end 102p at a proximal juncture 122p. In other words, a diameter D of the tubular body 108 at the intermediate portion 120 can be larger than a diameter Dp of either of the proximal end 102p and a diameter Dd the distal end 102d, though, in some embodiments, the tubular body 108 can include a uniform diameter extending therethrough. It will be appreciated that the diameters Dp, Dd of the proximal and distal ends 102p, 102d can be equal, though, in some embodiments Dp can be larger than Dd and vice versa. Further, a diameter of the elongate shaft along certain portions thereof can be configured to substantially match an inner diameter between opposed arms 16A, 16B or extension tabs 20 in order to prevent radially-inward deflection of the arms that might result in inadvertent separation of the receiver member 12 from the instrument 100. For example, the diameter of the elongate shaft 102 is illustrated as substantially similar to the inner diameter between the arms 16A, 16B or extension tabs 20 at locations 1402 and 1404 in FIG. 14.

As shown in FIG. 7, the intermediate portion 120 can include one or more mating features 124 that engage the sleeve 104 for selectively locking the elongate shaft 102 relative thereto. For example, the tubular body 108 can include a longitudinal groove 126 and a first partial circumferential groove 128 formed on a surface thereof. The longitudinal groove 126 and the first partial circumferential groove 128 can allow one or more portions of the sleeve 104 to engage with the elongate shaft 102 to couple the sleeve 104 thereto and guide relative movement between the two components. For example, in some embodiments, the grooves 126, 128 can receive one or more protrusions formed on an internal wall of the sleeve (e.g., a pin passing through a through-bore in the sidewall of the sleeve, as described in more detail below) that can guide the position of the sleeve 104 relative to the shaft 102, as discussed further below.

As shown, the longitudinal groove 126 can extend along a surface of the tubular body 108. For example, the longitudinal groove 126 can extend from a proximal portion of the elongate shaft 102 into the intermediate portion 120, though in some embodiments, the longitudinal groove 126 can be limited to the intermediate portion. As shown, the longitudinal groove 126 can be a substantially rectangular groove having a proximal end 126p and a distal end 126d, as shown in FIGS. 7 and 10, though other groove shapes or profiles can also be utilized. The distal end 126d of the longitudinal groove 102 can terminate at a first shoulder 130. The first shoulder 130 can be positioned along the tubular body 108 of the intermediate portion 120 to act as a stop against further distal advancement of the sleeve 104 relative to the shaft 102.

While a single longitudinal groove is shown, in some embodiments, the tubular body 108 can have one or more additional longitudinal grooves, e.g., parallel grooves formed around the circumference of the elongate shaft 102, to allow one or more additional features of the sleeve to extend through the plurality of grooves simultaneously to increase the strength of the coupling.

The first partial circumferential groove 128 can be offset from the longitudinal groove 126 along the tubular body 108 of the elongate shaft 102. As shown, the partial circumferential groove 128 can form a dogleg junction 129 at the first shoulder 130 with the radial groove 128 so that the grooves form the shape of an "L" or an inverted "L" (see FIG. 7). The first partial circumferential groove 128 can extend along a circumference of the elongate shaft 102 and receive objects (e.g., the protrusion or pin of the sleeve 104) that travel distally along the longitudinal groove 126 to the junction 129. Rotation of the elongate shaft 102 relative to an object located at the dogleg junction 129 can move an object traveling distally along the longitudinal groove 126 into the first partial circumferential groove 128. While a single partial circumferential groove 128 is shown, in some embodiments, the tubular body 108 can have a one or more other partial circumferential grooves formed therein, e.g., in embodiments where multiple longitudinal grooves are employed, as described above. In such embodiments, the various longitudinal grooves can be spaced appropriately to avoid interference of their associated partial circumferential grooves, e.g., two opposing longitudinal grooves with partial circumferential grooves that do not intersect or multiple partial circumferential grooves formed at longitudinally offset locations that connect with parallel longitudinal grooves of different lengths and receive protrusions or features formed on the sleeve 104 at different longitudinal positions.

The elongate shaft 102 can also include an additional, at least partial circumferential groove 132 formed therein. As shown, the at least partial circumferential groove 132 can include a reduced diameter relative to the intermediate portion 120 diameter D. The at least partial circumferential groove 132 can be formed between a first shoulder 130 and a second shoulder 134 formed along the tubular body 108 (see FIG. 7). The at least partial circumferential groove 132 can be configured to interface with one or more components of the instrument 100, e.g., the sleeve 104, to retain the orientation of the instrument in one or more positions.

Figure 8A:
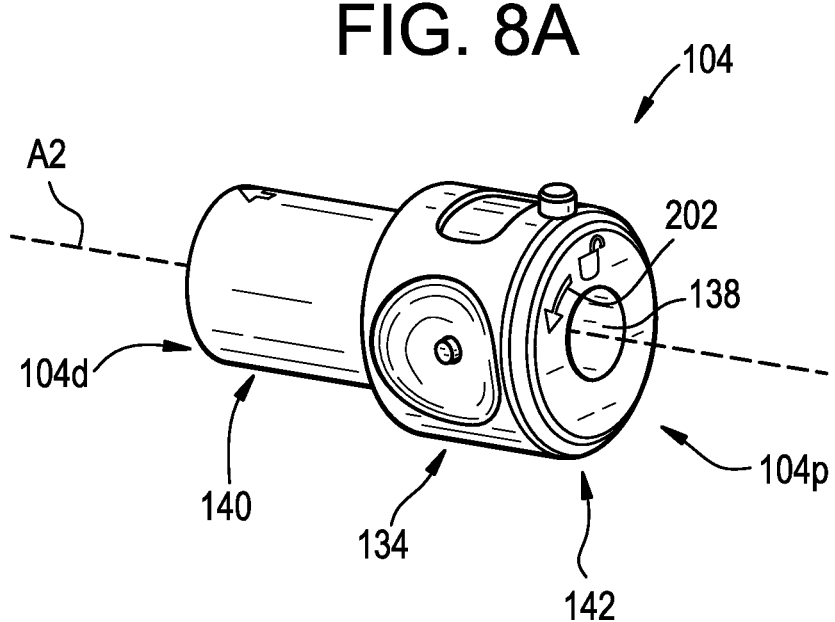
FIG. 8A is a rear perspective view of the sleeve of the device of FIG. 1.
Figure 8B:
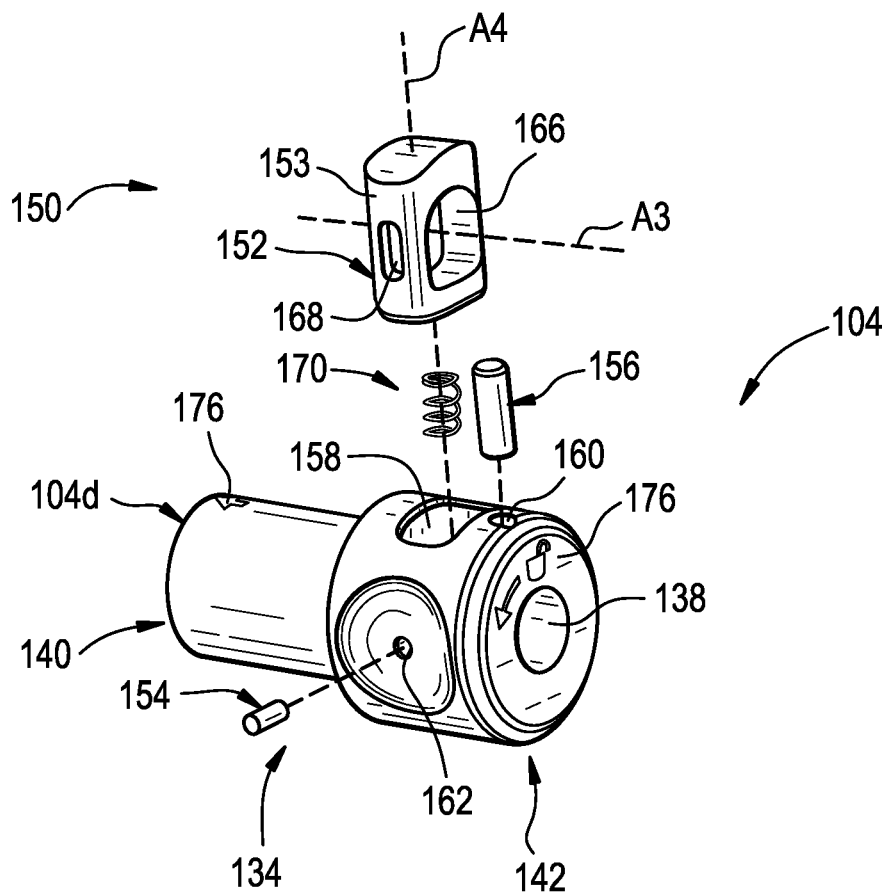
FIG. 8B is a rear exploded view of the sleeve of FIG. 8A.
Figure 8C:
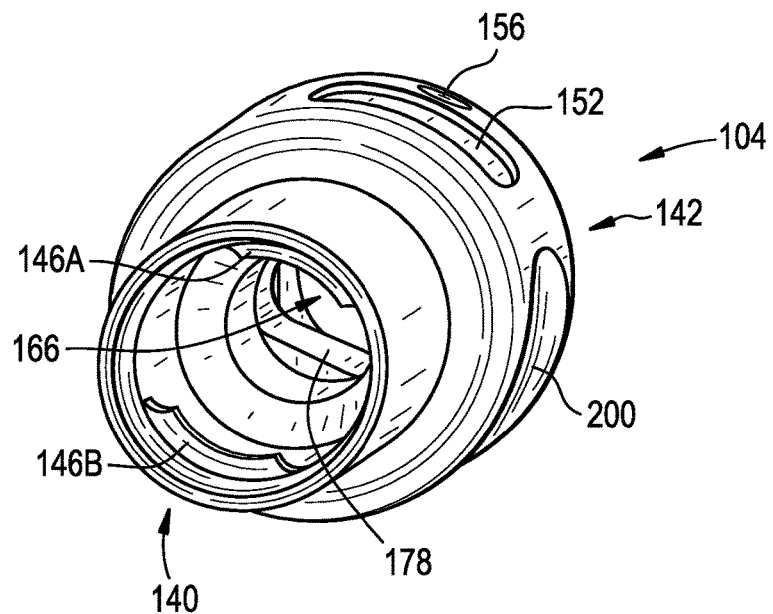
FIG. 8C is a front perspective view of the sleeve of FIG. 8A.

FIGS. 8A-8C illustrate the sleeve 104 of the instrument 100 in greater detail. As discussed above, the sleeve 104 can receive a portion of the elongate shaft 102 therethrough. The sleeve 104 can include a generally cylindrical body 134 having a channel or lumen 138 extending therethrough. The channel 138 can extend along a central longitudinal axis A2 of the sleeve 104 from a proximal end 104p of the body 134 to a distal end 104d of the body. As shown, the central longitudinal axis A2 of the sleeve 104 can substantially align with the central longitudinal axis A1 of the elongate body. The channel or lumen 138 can define one or more diameters D1 through which instruments, implants, or other objects, e.g., the elongate shaft 102, among others, can be inserted. In some embodiments, an interior surface of the channel 138 can include features for cooperating with another component, such as the elongate shaft 102 or a portion of an implant component, such as the receiver head 12.

The body 134 of the sleeve 104 can include a distal mating portion 140 and a proximal engagement portion 142. The distal mating portion 140 and the engagement portion 142 can share a common channel or lumen 138 within the sleeve 104, though the sections can define different lumen diameters. For example, a length of the channel 138 that extends through the proximal engagement portion 142 of the sleeve 104 can include a reduced diameter relative to the distal mating portion (see FIG. 10) that can be configured to receive the elongate shaft 104 therethrough. The distal mating portion 140 can include a portion having an enlarged diameter relative to the proximal engagement portion 142 to allow for implant components or parts thereof, e.g., spaced apart arms 16A, 16B of the receiver member 12, to be received in the space between the sleeve 104 and the elongate shaft 102, as discussed with respect to FIGS. 13 and 14 below.

Figure 13:
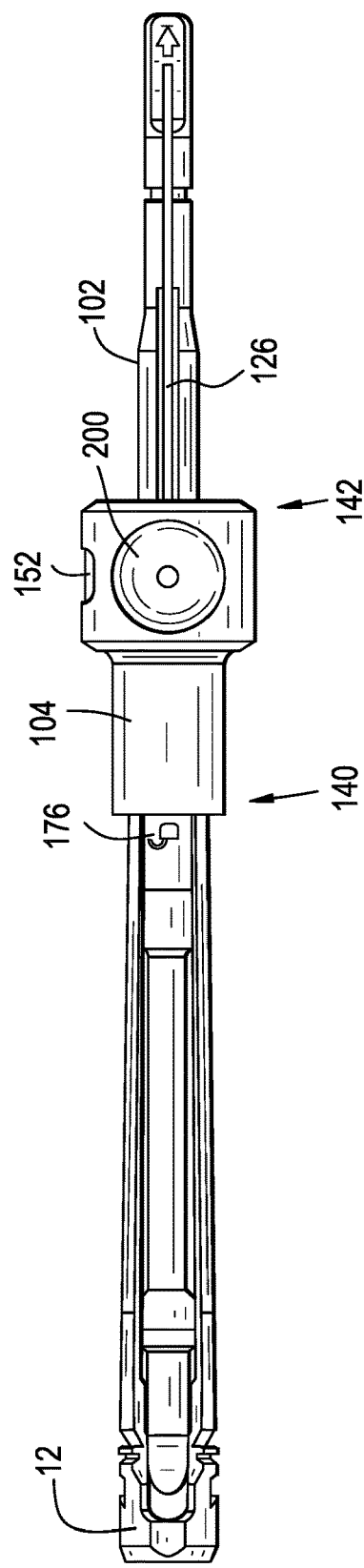
FIG. 13 is a top view of the device of FIG. 1 in a locked position coupled to a modular receiver member with extension tabs like that shown in FIG. 5.
Figure 14:
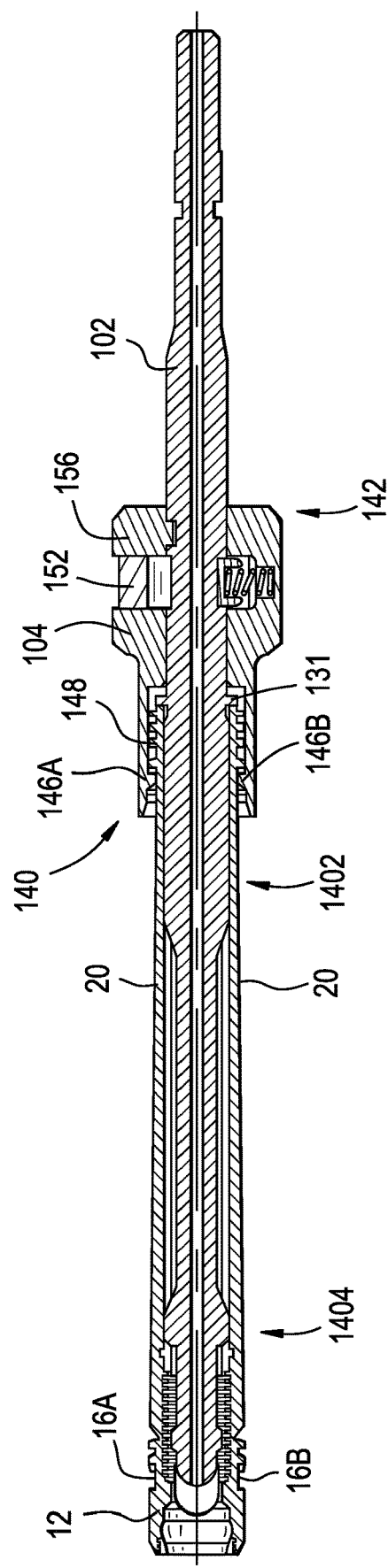
FIG. 14 is a top cross-sectional view of the device of FIG. 13.

The distal mating portion 140 can include one or more features for mating the sleeve 104 to an implant component or other object disposed therein. For example, the features can be a pair of opposed projections or shelves 146A, 146B that extend from an inner surface 148 of the mating portion 140 of the sleeve 104 into the channel 138 of the mating portion, as shown in FIGS. 8C and 10. For example, as shown in FIGS. 13 and 14, the features 146A, 146B can abut features formed on an implant component (e.g., extension tabs 20 or arms 16A, 16B of a receiver member 12), such as threads, lips, or other features, to prevent the component from backing out, or moving distally relative to, the distal end 104d of the sleeve 104, though the features 146A, 146B can also prevent proximal advancement of objects through the channel 138 of the sleeve 104 in some embodiments (e.g., if the features 146A, 146B were disposed in a valley between opposed protruding features formed on a component received within the lumen 138 of the sleeve 104). Further, the arms 146A, 146B can work in concert with the coupler 116 at the distal end of the elongate shaft 102 and a flange 131 that is configured to abut against a top or proximal-facing surface of the extension tabs 20 to fully constrain movement of the receiver member 12 relative to the instrument 100 when in the locked configuration. As shown, the features 146A, 146B can be formed on diametrically opposed portions of the inner surface 148 such that the features 146A, 146B can interface with diametrically opposed surfaces of an object, e.g., the opposed extended tabs 20 of a receiver member 12, as discussed further below. The features 146A, 146B can be fixed to sleeve 104 such that they rotate in tandem with the sleeve. For example, in some embodiments, rotation and/or manipulation of a position of the sleeve 104 can bring the features 146A, 146B into a position to mate to objects disposed within the lumen of the sleeve. Although two opposing protrusions, shelves, or other features 146A, 146B are shown, the mating portion 140 can include one or more additional features disposed around a circumference of the lumen.

Figure 9:
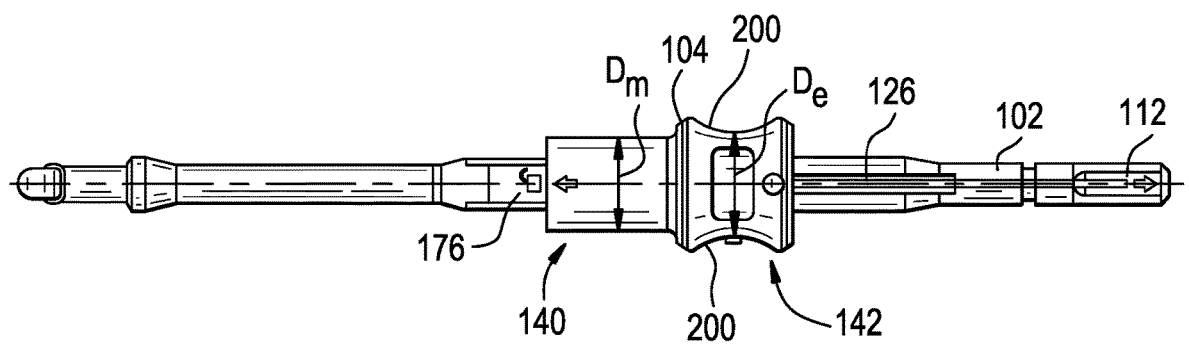
FIG. 9 is a top view of the device of FIG. 1 in an unlocked position.

As shown in FIG. 9, the proximal engagement portion 142 of the sleeve 104 can have a larger outer diameter De than a diameter Dm of the distal mating portion 140, though, in some embodiments, the diameter Dm of the distal mating portion 140 can be larger than that of the proximal engagement portion De, or the diameter of the sleeve 104 can be uniform throughout.

The elongate shaft 102 can move relative to the sleeve 104 in one or more degrees of freedom. For example, as shown, the engagement portion 142 can be positioned over the at least partial circumferential groove 132 formed in the elongate shaft 102 to couple the sleeve thereto. FIG. 8B illustrates the sleeve 104, and specifically the engagement portion 142, in greater detail. The engagement portion 142 can receive one or more linking components 150 for interfacing with the at least partial circumferential groove 132 of the elongate shaft 102. As shown, the linking components 150 can include a button 152, a positioning pin 154, and a guiding pin 156. The linking components 150 can be received in one or more recesses, through-holes, or bores formed in the engagement portion 142 to place the linking components 150 in communication with the channel or lumen 138. For example, as shown, the engagement portion 142 can include a recess 158 for receiving the button 152 therein, a recess 160 for receiving the guiding pin 156 therethrough, and a recess 162 for receiving the positioning pin 154 therethrough, though, in some embodiments, additional recesses can be formed in the engagement portion 142 and/or the distal mating portion 140. The interface between the linking components 150 disposed within the engagement portion 142 and the corresponding features of the elongate shaft 102 to promote interaction between the elongate shaft 102 and the sleeve 104 are discussed further below.

The button 152 can include a substantially rectangular body 153 having one or more channels 166 formed therein. As shown, the button 152 can be received in the corresponding recess 158 formed in the body 134 of the sleeve 104 to dispose the button therein. The button 152 can be received in the recess 158 to interface with one or more features of the elongate shaft 102 to allow for transmission of axial forces to any implant parts retained by the instrument 100. In some embodiments, the button 152 can be actuated to allow disassembly of the elongate shaft 102 from the sleeve 104, thereby disassembling the instrument for cleaning, sterilization, etc.

The button 152 can include a central channel 166 formed therein for allowing the elongate shaft 102 to pass therethrough. As shown, the central channel 166 can define a longitudinal axis A3 that extends through a width of the button that substantially aligns with one or more of the central longitudinal axes A1, A2 of the elongate shaft 102 and the sleeve 104 to allow the elongate shaft 102 to extend through the central channel 166. The central channel 166 can include at least one curved surface that can correspond to a shape of the elongate shaft 102 such that the central channel 166 forms a substantial negative of the elongate shaft 102 along at least a portion thereof. In some embodiments, the central channel 166 can be at least partially circular, oval, rectangular, square, oblong, or another shape configured to allow the elongate shaft 102 to pass therethrough.

The button 152 can include additional recesses formed in the body 153 thereof. For example, the button 152 can have a recess 168 formed in a lateral side surface thereof. As shown, the recess 168 can be formed in a surface that is substantially orthogonal to the central channel 166. In some embodiments, the recess 168 can be positioned such that objects disposed within the recess are not in communication with the central channel 166, though, in some embodiments, the recess can extend through the body 153 to be in communication with the central channel 166. The recess 168 can be sized and shaped to receive one of the linking components 150 therethrough, e.g., the positioning pin 154. The positioning pin 154 can travel within the recess 168 to limit movement of the button 152 along an axis A4 that is substantially perpendicular to the central longitudinal axis A3 of the central channel 166.

The button 152 can engage the elongate shaft 102 via a bias element (e.g., a coil spring) 170 disposed between the button 152 and the sleeve 104. For example, the button 152 can include a first recess 172 formed in a bottom surface thereof, as shown in FIG. 11. The first recess 172 can be sized and shaped to receive the bias element 170 therethrough. In some embodiments, the bias element 170 can be disposed between the first recess 172 and a second recess 174 that is formed in the body 134 of the sleeve 104.

As described above, the bias element 170 can urge the button 152 to move along the axis A4 that is substantially perpendicular to the axes A1, A2 of the elongate shaft 102 and the sleeve 104, respectively, between (i) a first position in which the button 152 engages the elongate shaft 102 to lock an orientation of the sleeve 104 relative to the elongate shaft 102, and (ii) a second position in which the button 152 disengages from the elongate shaft 102 to allow the sleeve 104 to translate and/or rotate relative to the elongate shaft 102 in one or more degrees of freedom, as discussed below. While a coil spring 170 is shown, various other bias elements can be used instead or in addition, such as leaf springs, wave springs, torsion springs, resilient compressible members, electromagnets, etc., can be used to allow the button to be depressed and recoil in the direction of axis A4.

The guiding pin 156 can be received within the recess 160 formed on the engagement portion 142, as shown, to guide movement of the sleeve along the elongate shaft. The guiding pin 156 can be a stationary pin that moves in tandem with the sleeve 104 relative to the elongate shaft 102, though, in some embodiments, the guiding pin can pivot and/or translate with respect to the elongate shaft 102. In still other embodiments, the guiding pin can be integrally formed with the sleeve 104 as a protrusion extending from an inner wall of the lumen 38. The guiding pin 156 can travel within the longitudinal groove 126 formed in the elongate shaft 102. As shown, the guiding pin 156 can extend through the engagement portion 142 into the channel or lumen 38 of the sleeve 104 to interface with the elongate shaft. Once so disposed, the guiding pin 156 can align with one or more of the longitudinal groove 126 and/or the partial circumferential groove 128 of the elongate shaft 102 to guide and limit translation and rotation of the elongate shaft 102 relative to the sleeve 104, e.g., allowing movement between locked and unlocked configurations of the instrument 100. The recesses 158, 160 can be angularly aligned about the longitudinal axis A2 such that an angular position of the button 152 and the guiding pin 156 relative to the elongate shaft 102 remains the same as the instrument 100 moves between unlocked and locked configurations.

The sleeve 104 and/or the elongate body 102 can include one or more indicators 176 that show whether the instrument is in an unlocked or locked position or configuration. For example, as shown in FIGS. 8A-8C, the body 134 can include labels or images 176 thereon to indicate the locked/unlocked status of the instrument 100. In some embodiments, the sleeve 104 can include a first image of a padlock in an unlocked or open position with an image of an arrow pointing in a counterclockwise direction. The padlock in the unlocked position can indicate that the instrument 100 can be unlocked by rotating the sleeve in the direction of the arrow. The sleeve 104 can also include an arrow 176 on the distal mating portion 140, as shown. This arrow 176 can align with an image of a padlock in an open or closed position along another portion of the instrument, such as the padlock in the open position on the elongate shaft 102 shown in FIG. 9, to illustrate that the instrument 100 is in the unlocked position. In some embodiments, the image on the elongate shaft 102 can be that of a padlock in a closed position, which would indicate that the instrument 100 is in the locked position when the arrow on the sleeve 104 aligns with the image. Other text or images can be used instead or in addition, such as text labels reading "open" and "closed," other drawings, etc.

The instrument 100 can include additional indicators for communicating the position of the instrument 100. For example, a position of the button 152 relative to the longitudinal groove 126 can inform the user as to whether the instrument 100 is in the unlocked position or in the locked position. As shown, when the button 152 is aligned with the longitudinal groove 126 of the elongate shaft 102, the instrument 100 is in the unlocked position, while when the button 152 is angularly offset from the longitudinal groove 126, the instrument 100 is in the locked position or at least in a transition toward the locked position. In some embodiments, a shape of the engagement portion 142 can also inform the user as to whether the instrument is in the unlocked position or in the locked position. For example, as shown in FIGS. 9, 10, 13, and 14, the engagement portion 142 can have a substantially cylindrical shape with opposed scalloped or cutout portions 200 that can align with the longitudinal groove 126 in the unlocked configuration and be angularly offset therefrom when in the locked configuration.

In use, the elongate shaft 102 can be advanced proximally through the mating portion 140 and into the engagement portion 142 to assemble the instrument, as shown in FIG. 6 above. During assembly, the sleeve 104 can be positioned such that the guiding pin 156 aligns with the longitudinal groove 126 to contact and/or otherwise engage the longitudinal groove. As the elongate shaft 102 continues to advance proximally through the sleeve 104, the elongate shaft 102 passes through the central channel 166 of the button 152 and out of the proximal end 104p of the sleeve 104. During advancement, the guiding pin 156 engages the proximal end 126p of the longitudinal groove 126 and slides distally therein. The elongate shaft 102 and/or the sleeve 104 can continue to move relative to one another until the guiding pin 156 is disposed at the distal end 126d of the longitudinal groove 126 and the button 152 engages the recessed portion 132 between the first and second shoulders 130, 134. In this position, the instrument 100 can engage a receiver member 12 like that shown in FIG. 5, as described further below.

FIGS. 9-12 illustrate the instrument 100 in an unlocked position, while FIGS. 13 and 14 illustrate the instrument in the locked position while engaging the extended tabs 16A, 16B of a receiver member 12 like the one shown in FIG. 5. Except as indicated below, steps of any described methods can be performed in various sequences, and one or more steps can be omitted or added. Further, a detailed description of every sequence of steps is omitted here for the sake of brevity. The instrument 100 can include an adjustment mechanism for docking, mating, and decoupling the instrument from one or more implant parts, as well as disassembling the components of the instrument. For example, the sleeve 104 can be rotated relative to the elongate body 102 to move the instrument 100 between (i) an unlocked position in which the instrument 100 is free to engage the tabs of the receiver member, and (ii) a locked position in which the instrument 100 engages the tabs of the receiver member to form a rigid connection with the receiver member and enable transmission of tensile and compressive forces during assembly of the receiver head to a bone screw shank. Assembly of the modular receiver member to the bone screw shank can occur prior to surgery, post-surgery, or intraoperatively to allow for rapid bone anchor assembly. The instrument in each of the unlocked and locked positions is shown and discussed in greater detail below.

FIGS. 9-12 illustrate the instrument 100 in the unlocked position, with the sleeve 104 being oriented relative to the elongate shaft 102 to allow the guiding pin 156 to be disposed in the longitudinal groove 126. As shown, the button 152 is disposed substantially perpendicular to the longitudinal groove 126 and the arrow 176 on the distal mating portion aligns with a padlock in the open position pictured on the elongate shaft 102 to clarify that the instrument 100 is in the unlocked position. In one embodiment, the elongate shaft distal coupler 116 can be urged into a U-shaped seat of a receiver member 12 while the sleeve 104 is disconnected from the elongate shaft 102 or disposed along a proximal portion thereof. The sleeve 104 can then be advanced distally along the elongate shaft 102 until the distal engagement portion 142 with its open distal end slides over the proximal end of the receiver member extension tabs 20. As shown in FIG. 10, the guiding pin 156 sits in a distal end 126d of the longitudinal groove 126, or in the dogleg junction 129 between the longitudinal groove 126 and the radial groove 128 in the unlocked position. Further, in the unlocked configuration the opposed inwardly projecting arms 146A, 146B formed on an inner surface of the sleeve 104 can be aligned with the gaps formed between the opposed extension tabs 20 of the receiver member, ensuring no interference between these components as the sleeve 104 slides distally over the proximal end of the tabs 20. As described above, the adjustment mechanism of the instrument 100 can allow the sleeve 104 to be rotatable relative to the elongate shaft 102 about the axis A2 to move between the unlocked position and the locked position once the components are properly positioned relative to one another along the longitudinal axis A2. For example, the sleeve 104 can be rotated in a clockwise direction, when viewed from a proximal perspective, to move the sleeve 104 from the unlocked position shown in FIG. 9 into the locked position shown in FIG. 13, though, in other embodiments, the direction of rotation can be reversed. Such rotation of the sleeve 104 relative to the elongate shaft 102 and receiver member 12 (which is held relative to the elongate shaft by the coupler 116) can allow the opposed arms 146A, 146B of the sleeve to interface with a notch, groove, protrusion, or other feature formed on an outer surface of the extension tabs 20 in order to help rigidly secure the receiver member 12 to the instrument 100. Further, the flange 131 formed on the elongate shaft 102 can abut against a proximal surface of the extension tabs 20 to further limit relative movement between the receiver member 12 and the instrument 100.

Figure 12:
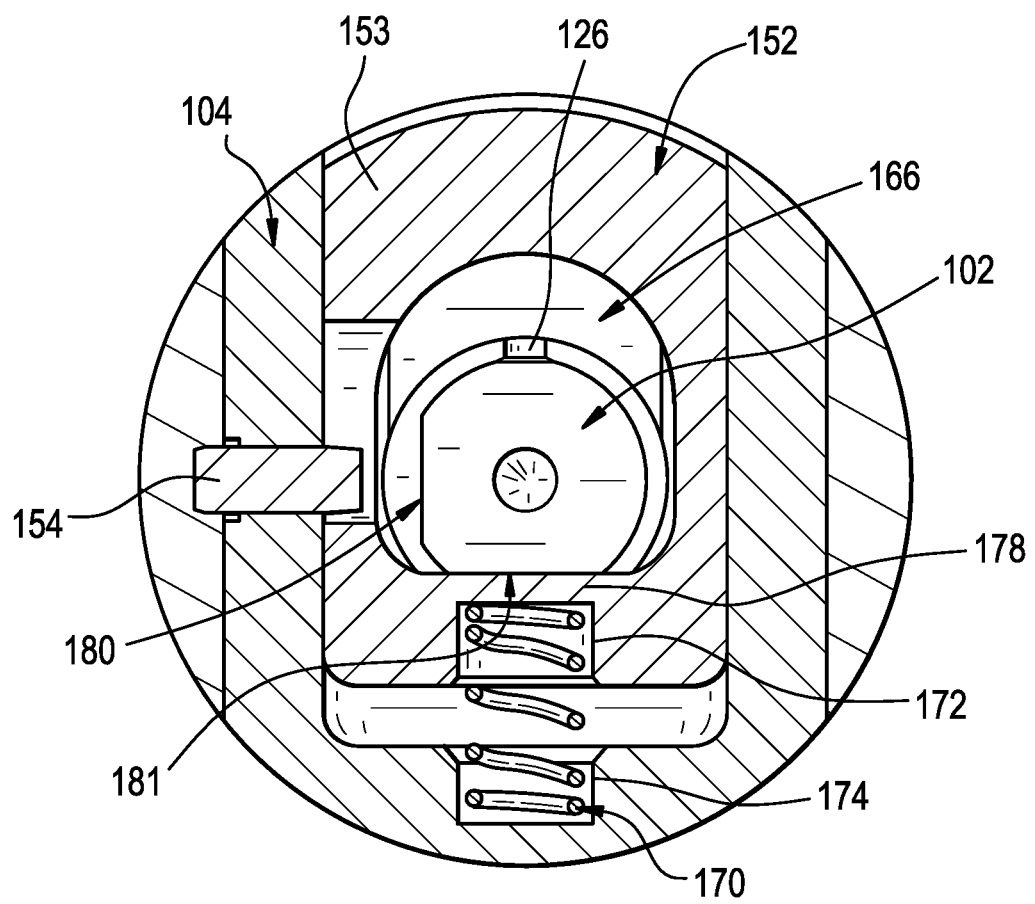
FIG. 12 is a detail transverse cross-sectional view of the device of FIG. 1 in an unlocked position.

FIGS. 11 and 12 illustrate the interface between the engagement portion 142 of the sleeve 104 and the elongate shaft 102 in greater detail in the unlocked position. As shown, the button 152 can include a flange 178 formed on the body 153. In some embodiments, the flange 178 can extend from the body 153 to interface with one or more features of the instrument 100, e.g., the elongate shaft 102, the sleeve 104, and so forth. For example, as shown, the flange 178 of the button 152 interfaces with the first and second shoulders 130, 134 that define the recessed portion 132 of the elongate shaft 102 to provide an axial stop that prevents further proximal and distal displacement of the elongate shaft relative to the sleeve. The interface between the flange 178 and the shoulders 130, 134 also allows the instrument 100 to transmit axial forces to an implant when mated thereto.

The bias element 170 disposed within the first spring recess 172 exerts a force onto the button 152 to urge the button in the direction of axis A4 such that the flange 178 sits in the recessed portion 132 of the elongate shaft 102. As discussed above, the recessed portion 132, which is disposed between the first and second shoulders 130, 134 along the length L of the elongate shaft 102, can include one or more flats 180, 181. The flats 180, 181 in the recessed portion 132 can serve as detents that provide preferred orientations of the sleeve 104 in each of the unlocked and locked positions (e.g., the sleeve 104 will preferentially move to align the flat face of the flange 178 with the closest flat 180, 181 when rotated). The flats 180, 181 can be positioned substantially perpendicularly to one another such that their orientation aligns with an orientation of the sleeve 104 in the unlocked and locked positions to allow the flange 178 to engage one of the flats in each of the locked and unlocked positions. For example, as shown in FIG. 12, the flange 178 of the button 152 engages the flat 181 along the elongate shaft 102 to help retain the orientation of the sleeve in the unlocked position. In some embodiments, the elongate shaft can include a plurality of flats, including first and second flats 180, 181 as illustrated, but also including any number of flats that can be utilized to provide any number of rotational stops or detents as necessary or desired.

As a rotational force is imparted onto the sleeve 104, the guiding pin 156 travels out of the dogleg junction 129 connection between the longitudinal groove 126 and the partial circumferential groove 128 to become disposed within the partial circumferential groove 126. The guiding pin 156 travels along a circumference of the elongate shaft 126 when moving from the dogleg junction 129 into the partial circumferential groove 128 in the direction of rotation of the sleeve 104. Once inside the partial circumferential groove 126, the guiding pin 156 can provide a rotational stop to lock the sleeve 104 with respect to the elongate shaft 102 to position the instrument 100 in the locked position. For example, the guiding pin 156 can ride in the partial circumferential groove 128 when the instrument is moved between the unlocked position and the locked position while preventing over-rotation of the sleeve 104 with respect to the elongate shaft 102. The sleeve 104 can rotate approximately a quarter-turn, or 90 degrees, from the unlocked position to the locked position, though, in some embodiments, the instrument 100 can be in a locked position after a rotation of a different degree, e.g., from about 45 degrees to about 110 degrees in certain embodiments, though other values are possible. Further rotation of the sleeve 104 relative to the elongate shaft 102 is prevented by the guiding pin 156 abutting an end of the partial circumferential groove 128 to resist such rotation. Once the required rotation is completed, the flange 178 of the button 152 can engage the flat 180 of the elongate shaft, which can help retain the sleeve 104 in the locked position. Further, as soon as a user rotates the sleeve 104 sufficiently to pass the flange away from the flat 181 and bring it closer to the flat 180, the interaction of the components and their complementary shapes can urge the sleeve 104 to continue to the locked configuration where the flat 180 squarely abuts the flange 178.

FIGS. 13 and 14 illustrate the instrument 100 in the locked position. As shown, the sleeve 104 is positioned approximately a quarter-turn relative to the elongate shaft 102 such that the arrow 176 on the engagement portion 142 is offset from the padlock icon on the shaft 102 and the button 152 is offset from the longitudinal groove 126. The receiver member 12 can be disposed between the sleeve 104 and the elongate shaft 102 to mate the extended tabs 16A, 16B of the receiver member 12 to the instrument 100. The guiding pin 156 can be disposed within the partial circumferential groove 128 to serve as a rotational stop and prevent over rotation of the sleeve 104 relative to the shaft 102. As shown in FIG. 14, rotation of the sleeve 104 into the locked configuration can position the fixed arms 146A, 146B of the mating portion 140 along a surface of the extended tabs 16A, 16B so as to prevent the tabs from backing out of the mating portion 140, thereby rigidly securing the receiver member 12 to the instrument 100. The button 152 can remain aligned with the recessed portion 132 of the shaft 102 disposed between the shoulders 130, 134 such that forces imparted to the shaft will be transmitted to the rigidly-coupled receiver member 12.

The sleeve 104 and the elongate shaft 102 can be disassembled for cleaning after use. For example, to disassemble the instrument, the sleeve 104 can be moved in an opposite direction, e.g., counterclockwise, as shown by the arrow and unlock indication 202 in FIG. 8B, to return the instrument 100 to the unlocked position from the locked position. This movement rotates the arms 146A, 146B of the mating portion 140 out of engagement with the extended tabs 16A, 16B of the receiver member 12 to allow the receiver member to decouple from the instrument 100. The rotation also brings the guiding pin 156 out of the partial circumferential groove 126 through the dogleg junction 129 and back into the distal end 126d of the longitudinal groove 126. In the unlocked position, the button 152 can be depressed to counter the urging force of the biasing element 170 such that the flange 178 no longer engages either of the flats 180, 181 of the recessed portion 132. As the button 152 is depressed further, the flange 178 is brought out of the recessed portion 132 such that the flange 178 no longer interferes with either of the first and second shoulders 130, 134 that define the recessed portion 132. With the button 152 no longer interfacing with the first and second shoulders 130, 134, any axial stop is cleared such that the elongate shaft 102 can translate relative to the sleeve 104. The elongate shaft 102 can be advanced out of the sleeve 104 to disassemble from the sleeve. While the elongate shaft 102 can be advanced distally out of the engagement portion 142, in some embodiments, the shaft 102 can advance through the mating portion 140 to disassemble from the sleeve 104.

Figure 15:
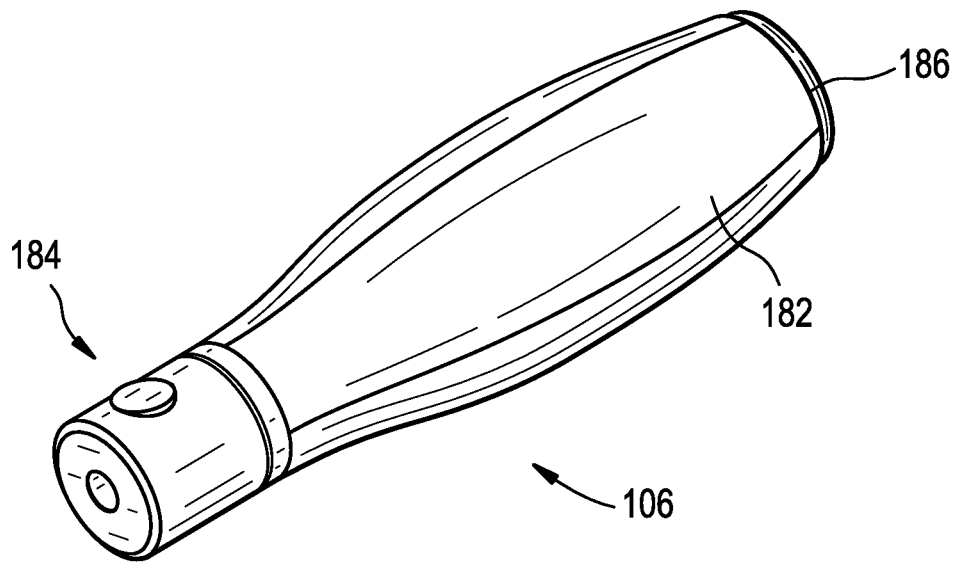
FIG. 15 is a front perspective view of the handle of FIG. 2.

FIG. 15 illustrates a handle 106 of the instrument 100 that can be used with the above-described elongate shaft and sleeve assembly. The handle 106 can be attached to the assembly of the elongate shaft 102 and the sleeve 104 to facilitate manipulation of the instrument by a user. For example, the handle 106 can be used to impart an axial load to instrument parts. As shown, the handle 106 can include a handle body 182, a modular activator 184, and a cap 186. The handle 106 can receive a proximal end of the elongate shaft 102 therein to attach the handle 106 to the instrument 100.

Figure 16:
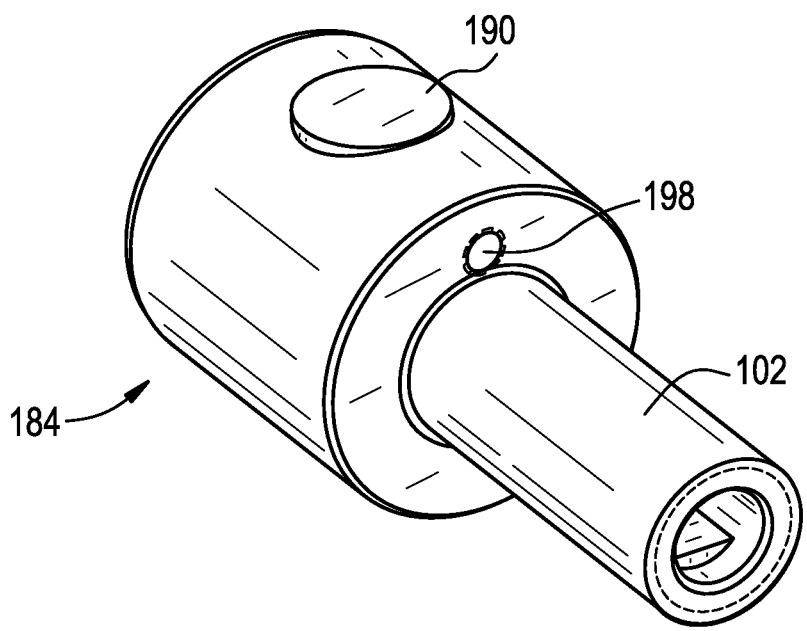
FIG. 16 is a front perspective view of a modular actuator of the handle of FIG. 16.
Figure 17:
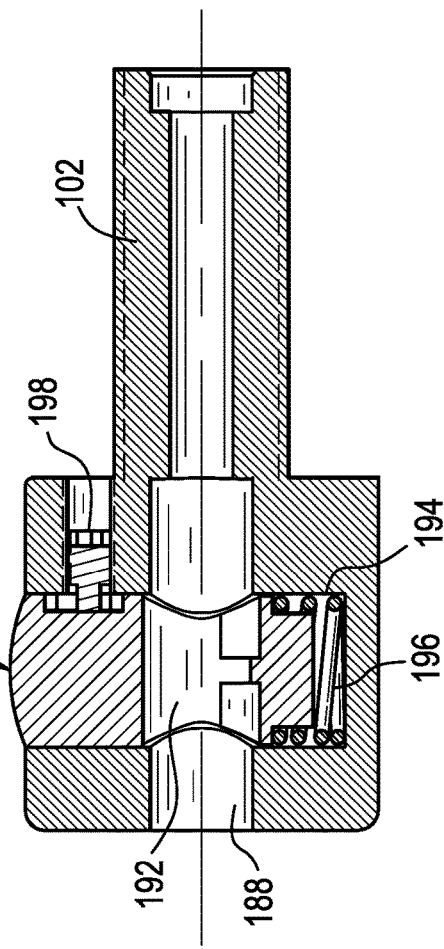
FIG. 17 is a side cross-sectional view of the modular actuator of FIG. 17 having an elongate shaft disposed therein.
Figure 18:
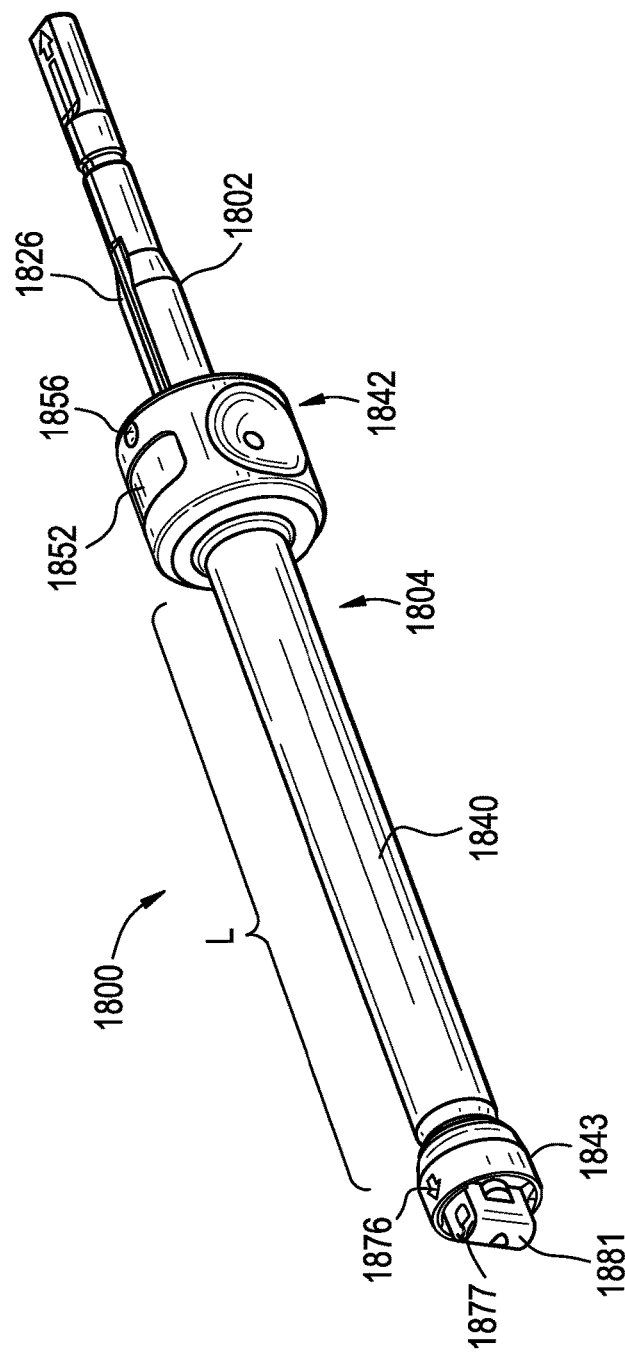
FIG. 18 is a front perspective view of another embodiment of a modular implant inserter.

FIGS. 16 and 17 illustrate the modular activator 184 of the handle 106 in greater detail. As shown, the modular activator 184 can include a through bore 188 for receiving the elongate shaft 102 therethrough and a push button 190 for attaching and detaching to the elongate shaft 102. The push button 190 can include a channel 192 that aligns with the through bore 188 to receive the elongate shaft 102 therethrough. As shown, the push button 190 can be disposed within a recess 194 of the handle that runs substantially perpendicular to the through bore 188. A biasing member 196 can be disposed within the recess 194 to urge the push button 190 upward (in the view of FIG. 17) from the handle 106 to offset the channel 192 of the button 190 from the through bore 188 to lock an object, e.g., the elongate shaft 102, disposed within the through bore 188. A screw 198 can retain the push button 190 within the modular activator 184.

In use, the elongate shaft 102 can be received within the through bore 188 of the activator 184 and advance therethrough to attach the elongate shaft 102 to the handle 106. To receive the elongate shaft 102, the push button 190 can be depressed to counteract the biasing force of the biasing member 196 to align the channel 192 of the push button 190 with the through bore 188 to allow the elongate shaft 102 to extend therethrough. To detach the handle 106 from the elongate shaft 102 after use, the push button 190 can be depressed to align the channel 192 of the button with the through bore 188 and enable translation of the elongate shaft 102 relative to the handle 106 out of the through bore 188. The handle 106 can then be used to attach to another elongate shaft 102 or removed for cleaning. In other embodiments, the handle can have a different shape (e.g., a laterally-extending "T" shape) or a plurality of handles can be provided to fit procedural need and/or user preference.

FIGS. 18-22 illustrate another embodiment of an instrument 200 that can be used for modular assembly of surgical devices. The structure and function of the instrument can be substantially the same as that of the embodiments described above, and therefore a detailed description is omitted here for the sake of brevity.

The instrument 1800 can include a sleeve 1804 disposed over an elongate shaft 1802 that can be coupled to a handle 2006, as shown in FIG. 20. The instrument can be used to mate to a polyaxial head of a receiver member, such as the receiver member 12 shown in FIGS. 3 and 4. As discussed above, the receiver member 12 can be without any extension tabs 20 or, in some embodiments, the extension tabs 20 can be smaller than the extended tabs 20 of the receiver member 12 of FIG. 5. Accordingly, the instrument 1800 can be adapted to couple to a receiver member 12 having no extension tabs (e.g., as shown in FIG. 3) or shorter extension tabs (e.g., as shown in FIG. 4) by including a sleeve 1804 with a mating portion 1840 having a length L that extends along the length of the elongate shaft towards the receiver member 12 to mate the sleeve 1804 to the receiver head 12 or short extension tabs 20.

Figure 19:
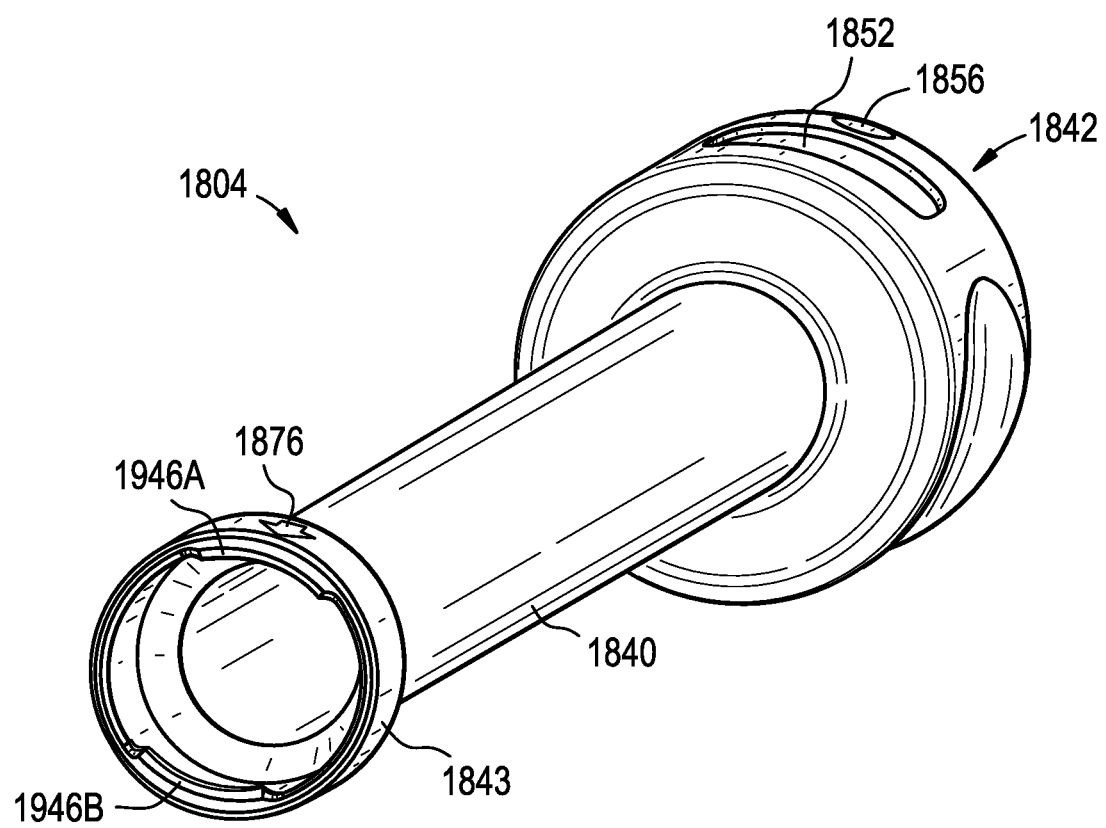
FIG. 19 is a front perspective view of the sleeve assembly of the device of FIG. 18.
Figure 22:
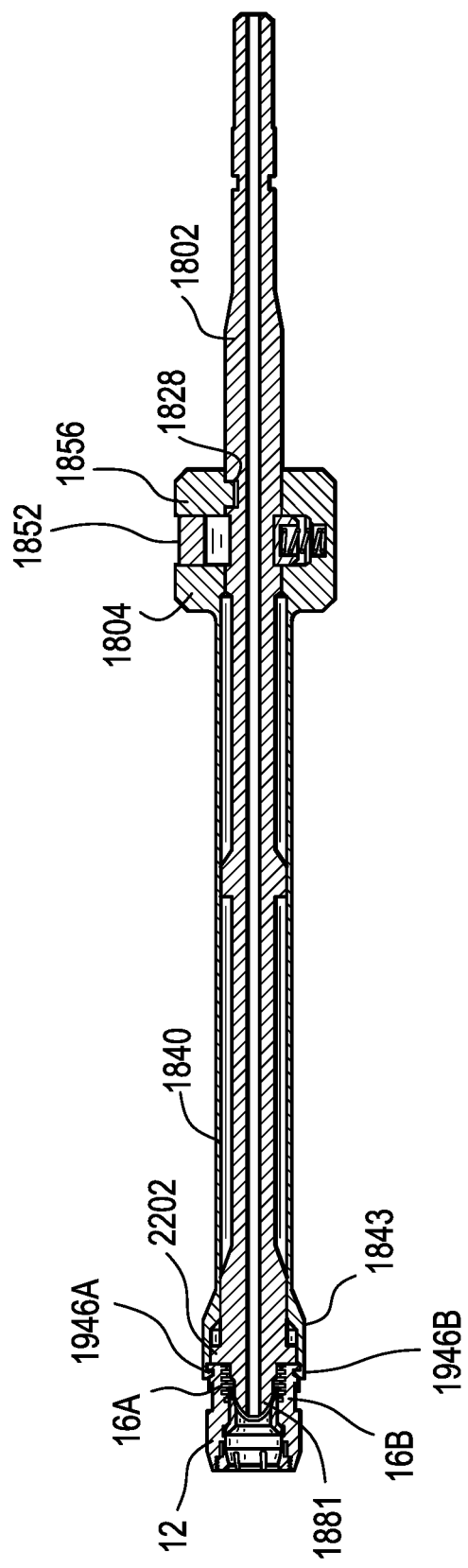
FIG. 22 is a top cross-sectional view of the assembly of FIG. 21.

As shown, a mating portion 1840 of the sleeve 1804 can taper to a coupling member 1843 configured to receive the polyaxial head of the receiver member 12 therein. The coupling member 1843 can include a pair of arms 1946A, 1946B that can be received in a notch or other feature formed on a surface of the receiver member 12 to help couple the instrument 1800 to the receiver member, as shown in FIG. 22. More particularly, and as shown in FIG. 19, the arms 1946A, 1946B can extend inward from a cylindrical surface of the coupling member 1843 and can extend around a partial circumference of the surface to allow gaps therebetween. A receiver head 12 can be inserted into the open distal end of the coupling member 1843 in a manner where the opposed arms 16A, 16B or short extension tabs 20 pass through the gaps between the arms 1946A, 1946B. Further, a distal end 1881 of the elongate shaft 1802 can be configured to seat within the U-shaped opening formed between the opposed arms 16A, 16B of the receiver member 12. This can prevent unintended rotation of the receiver member 12 relative to the elongate shaft 1802 and sleeve 1804. Similar to the instrument 100 described above, such insertion can take place when the instrument 1800 is in an unlocked configuration, ultimately arriving at a configuration like that shown in FIG. 20. While the proximal end of the receiver member is disposed within the open distal end of the coupling member 1843, the sleeve 1804 can be rotated relative to the elongate shaft 1802 and receiver member 12 to a locked configuration. This can rotate the arms 1946A, 1946B into engagement with a slot, notch, or other feature formed on an outer surface of the opposed arms 16A, 16B of the receiver member 12, as shown in FIGS. 21 and 22. As can be seen in the cross-sectional view of FIG. 22, the receiver member 12 can be securely and rigidly secured to the instrument 1800 in the locked configuration by opposing forces from the arms 1946A, 1946B, the distal end of the elongate shaft 1881, and a flange 1883 formed on a distal portion of the elongate shaft 1802 that abuts a top surface of the receiver member 12.

Similar to the instrument 100 described above, the mating portion 1840 can include an arrow or other indicator 1876 disposed thereon that can point to a padlock in the open position or other indicator 1877 on the elongate shaft 1802 to denote the instrument being in the unlocked position. As noted, the sleeve 1804 can be rotated to lock the instrument 1800 to mate the receiver member 12 thereto. Further, to detach the instrument 1800 from the receiver member 12, the sleeve 1804 can be moved in the opposite direction into the unlocked position. In this manner, a primary differentiator between the device 100 and the device 1800 can be the length L of the mating portion 1840, which can be extended to reach the receiver member 12 having no extension tabs or short extension tabs in comparison to the short mating portion 140 of the sleeve 104 in the instrument 100. An engagement portion 1842 of the sleeve 1804 can function in substantially the same way as the engagement portion 142 of the sleeve 104 in the instrument 100, e.g., by utilizing a guiding pin 1856 that rides within a longitudinal slot 1826 and partial circumferential slot 1828 formed in the elongate shaft 1802, as well as a spring-biased button 1852 with a central passage and flat surface that can engage an at least partial circumferential groove or recessed portion of the elongate shaft with flats or other features to guide the instrument between locked and unlocked configurations.

The devices, systems, and methods disclosed herein can be used in minimally-invasive surgery and/or open surgery. As noted above, any of a variety of surgical procedures can be performed utilizing the surgical instruments described herein, including various orthopedic procedures, such as knee surgery, spine surgery, shoulder surgery, hip surgery, etc., as well as general modular coupling of implant parts that might be applicable to a wide range of surgical procedures. Further, while the devices and methods disclosed herein are generally described in the context of surgery on a human patient, it will be appreciated that the methods and devices disclosed herein can be used in any of a variety of surgical procedures with any human or animal subject, or in non-surgical procedures.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely example embodiments, various other methods that include additional steps or include fewer steps are also within the scope of the present disclosure.

The instruments, devices, and systems disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned device, are all within the scope of the present disclosure.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

The embodiments of the present disclosure described above are intended to be examples; numerous variations and modifications are possible and within the scope of this disclosure. Accordingly, the disclosure is not to be limited by what has been particularly shown and described. All publications and references cited herein are expressly incorporated by reference in their entirety.

The invention claimed is:

1. A surgical instrument, comprising:
   an elongate shaft that terminates in a distal end that is configured to engage a modular structure, the elongate shaft having a longitudinal groove formed along a portion thereof, a first partial circumferential groove that intersects with a distal end of the longitudinal groove, and a second at least partial circumferential groove formed distal to the first partial circumferential groove; and
   a sleeve configured to be disposed over the elongate shaft, the sleeve including a protrusion extending from an internal wall thereof that is configured to be received within the longitudinal groove of the elongate shaft to constrain movement of the sleeve relative to the shaft when the sleeve is disposed over the elongate shaft;
   wherein the sleeve includes a lock configured to interface with the second at least partial circumferential groove when the protrusion is disposed in the first partial circumferential groove to further selectively constrain both axial and rotational movement of the sleeve relative to the shaft.

2. The instrument of claim 1, wherein the lock includes a button disposed within a recess of the sleeve and configured to translate radially relative to the sleeve and elongate shaft between a locked position and an unlocked position.

3. The instrument of claim 2, wherein the button is biased toward the locked position.

4. The instrument of claim 2, wherein the button includes a through-bore configured to receive the elongate shaft therethrough.

5. The instrument of claim 1, wherein the second at least partial circumferential groove includes a plurality of flat portions angularly offset from one another to define a plurality of rotational positions of the shaft relative to the sleeve.

6. The instrument of claim 5, wherein the plurality of flat portions includes a first flat portion and a second flat portion that define first and second rotational positions of the shaft relative to the sleeve.

7. The instrument of claim 5, wherein the lock includes a flat portion configured to abut one of the plurality of flat portions of the second at least partial circumferential groove to maintain the shaft at one of the plurality of rotational positions relative to the sleeve.

8. The instrument of claim 1, further comprising a handle configured to couple to a proximal portion of the elongate shaft to facilitate manipulation of the instrument.

9. The instrument of claim 1, wherein the sleeve and the elongate shaft are configured to engage one or more objects therebetween to form a rigid connection with the one or more objects.

10. The instrument of claim 9, wherein the sleeve further comprises a pair of arms to engage the objects when disposed between the elongate shaft and the sleeve.

11. The instrument of claim 10, wherein the object comprises one or more extended tabs of a receiver head.

12. The instrument of claim 1, wherein the second at least partial circumferential groove further comprises a pair of flats positioned substantially perpendicularly to one another with a remainder of the partial circumferential groove being substantially cylindrical.

13. A surgical instrument, comprising:
   an elongate shaft that terminates in a distal end that is configured to engage a modular structure, the elongate shaft having a longitudinal groove formed along a portion thereof, a first partial circumferential groove that intersects with a distal end of the longitudinal groove, and a second circumferential groove formed distal to the first partial circumferential groove; and
   a sleeve configured to be disposed over the elongate shaft;
   a pin configured to be received within a through-bore of the sleeve such that the pin extends into an inner lumen of the sleeve and can be received in the longitudinal groove and first partial circumferential groove of the elongate shaft to constrain relative movement of the sleeve and the elongate shaft when the sleeve is disposed over the elongate shaft; and
   a button received within a recess of the sleeve and configured to translate radially relative thereto, the button including a through-bore formed therein that is configured to receive the elongate shaft therethrough when the sleeve is disposed over the elongate shaft;
   wherein the button is configured to be disposed within the second circumferential groove of the elongate shaft and further constrain relative movement of the elongate shaft and sleeve when the pin is received in the first partial circumferential groove of the elongate shaft.

14. The instrument of claim 13, wherein the sleeve further includes first and second partial circumferential protrusions formed on a wall of the inner lumen of the sleeve.

15. The instrument of claim 13, wherein the button is biased radially outward relative to the sleeve.

16. The instrument of claim 13, wherein the second circumferential groove includes a plurality of flat portions angularly offset from one another to define a plurality of rotational positions of the shaft relative to the sleeve.

17. The instrument of claim 16, wherein the plurality of flat portions includes a first flat portion and a second flat portion that define first and second rotational positions of the shaft relative to the sleeve.

18. The instrument of claim 16, wherein the button includes a flat portion configured to abut one of the plurality of flat portions of the second circumferential groove to maintain the shaft at one of the plurality of rotational positions relative to the sleeve.

19. The instrument of claim 13, wherein the sleeve and the elongate shaft are configured to engage one or more objects therebetween to form a rigid connection with the one or more objects.

20. A method for coupling an instrument to an object, the method comprising:
   advancing a sleeve over an elongate shaft such that a protrusion extending from an internal wall of the sleeve travels within a longitudinal groove formed in the elongate shaft;
   positioning an object such that a portion of the object is disposed between the sleeve and the elongate shaft; and
   rotating the sleeve relative to the elongate shaft such that the protrusion travels within a partial circumferential groove formed in the elongate shaft that intersects with a distal end of the longitudinal groove to prevent relative movement between the object and the instrument,
   wherein rotating the sleeve relative to the elongate shaft includes passing a flange away from a first flat and towards a second flat, the sleeve being urged to continue rotating to a configuration where the second flat squarely abuts the flange.

21. The method of claim 20, wherein the sleeve is advanced over the elongate shaft to a position where the protrusion is disposed at an intersection of the longitudinal groove and the partial circumferential groove, and a lock of the sleeve is disposed in a second at least partial circumferential groove formed in the elongate shaft distal to the partial circumferential groove.

22. The method of claim 21, wherein:
   the second at least partial circumferential groove includes a plurality of flat portions angularly offset from one another to define a plurality of rotational positions of the shaft relative to the sleeve;
   the lock includes a flat portion configured to abut one of the plurality of flat portions of the second at least partial circumferential groove to maintain the shaft at one of the plurality of rotational positions relative to the sleeve; and
   rotating the sleeve relative to the elongate shaft includes rotating the sleeve between a first of the plurality of rotational positions and a second of the plurality of rotational positions.

23. The method of claim 21, further comprising actuating the lock of the sleeve to move the lock out of the second at least partial circumferential groove formed in the elongate shaft.

24. The method of claim 20, wherein positioning the object includes contacting the object with a pair of arms extending from the sleeve.

25. The method of claim 20, wherein the distal end of the longitudinal groove terminates at the partial circumferential groove.

* * * * *